(12) United States Patent
Sutton

(10) Patent No.: US 7,959,490 B2
(45) Date of Patent: Jun. 14, 2011

(54) ORTHOPAEDIC COMPONENT MANUFACTURING METHOD AND EQUIPMENT

(75) Inventor: Jeffrey K. Sutton, Medway, MA (US)

(73) Assignee: DePuy Products, Inc., Warsaw, IN (US)

(*) Notice: Subject to any disclaimer, the term of this patent is extended or adjusted under 35 U.S.C. 154(b) by 0 days.

(21) Appl. No.: 11/540,167

(22) Filed: Sep. 29, 2006

(65) Prior Publication Data

US 2007/0107182 A1 May 17, 2007

Related U.S. Application Data

(60) Provisional application No. 60/731,791, filed on Oct. 31, 2005.

(51) Int. Cl.
*B24B 49/00* (2006.01)
(52) U.S. Cl. ............................ 451/5; 451/60
(58) Field of Classification Search .................. 451/5, 6, 451/28, 35, 36, 38, 60, 104, 106
See application file for complete search history.

(56) References Cited

U.S. PATENT DOCUMENTS

| | | | |
|---|---|---|---|
| 5,449,313 A | 9/1995 | Kordonsky et al. | |
| 5,616,066 A * | 4/1997 | Jacobs et al. | 451/36 |
| 5,690,284 A | 11/1997 | Murray | |
| 5,951,369 A | 9/1999 | Kordonski et al. | |
| 5,971,835 A * | 10/1999 | Kordonski et al. | 451/38 |
| 6,106,380 A | 8/2000 | Jacobs et al. | |
| 6,267,651 B1 | 7/2001 | Kordonski et al. | |
| 6,332,829 B1 | 12/2001 | Trommer | |
| 6,402,978 B1 | 6/2002 | Levin | |
| 6,413,441 B1 | 7/2002 | Levin | |
| 6,503,414 B1 | 1/2003 | Kordonsky et al. | |
| 6,506,102 B2 * | 1/2003 | Kordonski et al. | 451/64 |
| 6,561,874 B1 | 5/2003 | Kordonski | |
| 6,719,611 B2 | 4/2004 | Kordonski et al. | |
| 6,746,310 B2 | 6/2004 | Tricard et al. | |
| 6,776,688 B2 | 8/2004 | Kim et al. | |
| 6,893,322 B2 | 5/2005 | Kordonski et al. | |
| 6,955,589 B2 * | 10/2005 | Kordonski et al. | 451/60 |

(Continued)

OTHER PUBLICATIONS

Tricard et al., *Sub-Aperture Approaches for Asphere Polishing and Metrology*, Invited Talk, Photonics Asia (Nov. 8-11, 2004) (16 pages).

(Continued)

*Primary Examiner* — Dung Van Nguyen
(74) *Attorney, Agent, or Firm* — Maginot, Moore & Beck

(57) ABSTRACT

A system for use in preparing an articulating surface of a component of an orthopaedic implant is provided. The system includes a magnetorheological polishing fluid including a carrier fluid and a plurality of particles suspendable in said carrier fluid. The system also includes a vessel for containing the Magnetorheological polishing fluid. The system also includes a mechanism for delivering the fluid to form a polishing zone and a holder for securing the component and for moveably positioning the articulating surface of the component relative to the polishing zone. The system further includes a controller for determining the rate of material removal from the object, for determining the direction and velocity of movement of the polishing zone relative to the object and for determining the number of cycles of polishing required.

3 Claims, 29 Drawing Sheets

U.S. PATENT DOCUMENTS

| | | |
|---|---|---|
| 6,956,657 B2 | 10/2005 | Golini et al. |
| 7,156,724 B2 | 1/2007 | Kordonski et al. |
| 7,173,691 B2 | 2/2007 | Murphy et al. |
| 7,261,616 B2 | 8/2007 | Kordonsky et al. |
| 7,297,290 B2 * | 11/2007 | Fuchs et al. ............ 252/62.54 |
| 7,433,057 B2 | 10/2008 | Murphy et al. |
| 2003/0087585 A1 | 5/2003 | Kordonsky et al. |
| 2004/0192171 A1 | 9/2004 | Koike |
| 2004/0266319 A1 | 12/2004 | Kordonski et al. |
| 2005/0079812 A1 | 4/2005 | Bechtold |

OTHER PUBLICATIONS

M.R. Oliver, *Chemcal-Mechanical Planarization of Semiconductor Material*, Springer-Verlag Berlin Heidelberg (2004).

Internet article entitled "Microwave Plasma Synthesis of Encapsulated Metal Nanopowders" by Joseph Lik Hang Chau; published at least as early as Sep. 28, 2006; 2 pages.

Internet pages or brochure from QED Technologies entitled "Technology, How It Works"; published at least as early as Sep. 28, 2006; 3 pages.

* cited by examiner

ORTHOPAEDIC COMPONENT MANUFACTURING METHOD AND EQUIPMENT

CROSS REFERENCE TO RELATED APPLICATIONS

This application is a Utility Patent Application of Provisional Patent Application, U.S. Patent Application No. 60/731,791 titled "ORTHOPAEDIC COMPONENT MANUFACTURING METHOD AND EQUIPMENT" filed Oct. 31, 2005. This application claims priority of Provisional Patent Application, U.S. Patent Application No. 60/731,791 titled "ORTHOPAEDIC COMPONENT MANUFACTURING METHOD AND EQUIPMENT" filed Oct. 31, 2005. U.S. Patent Application No. 60/731,791 is hereby incorporated by reference herein in its entirety.

TECHNICAL FIELD OF THE INVENTION

The present invention relates generally to the field of orthopaedics, and more particularly, to an implant for use in arthroplasty.

BACKGROUND OF THE INVENTION

The skeletal system includes many long bones that extend from the human torso. These long bones include the femur, fibula, tibia, humerus, radius and ulna.

A joint within the human body forms a juncture between two or more bones or other skeletal parts. The ankle, hip, knee, shoulder, elbow and wrist are just a few examples of the multitude of joints found within the body. As should be apparent from the above list of examples of joints, many of the joints permit relative motion between the bones. For example, the motion of sliding, gliding, and hinge or ball and socket movements may be had by a joint. For example, the ankle permits a hinge movement, the knee allows for a combination of gliding and hinge movements and the shoulder and hip permit movement through a ball and socket arrangement.

The joints in the body are stressed or can be damaged in a variety of ways. For example, gradual wear and tear is imposed on the joints through the continuous use of a joint over the years. The joints that permit motion have cartilage positioned between the bones providing lubrication to the motion and also absorbing some of the forces direct to the joint. Over time, the normal use of a joint may wear down the cartilage and bring the moving bones in a direct contact with each other. In contrast, in normal use, a trauma to a joint, such as the delivery of a large force, from an accident, for example, an automobile accident, may cause considerable damage to the bones, the cartilage or to other connective tissue such as tendons or ligaments.

Arthropathy, a term referring to a disease of the joint, is another way in which a joint may become damaged. Perhaps the best known joint disease is arthritis, which is generally referred to a disease or inflammation of a joint that results in pain, swelling, stiffness, instability, and often deformity.

There are many different forms of arthritis, with osteoarthritis being the most common and resulting from the wear and tear of a cartilage within a joint. Another type of arthritis is osteonecrosis, which is caused by the death of a part of the bone due to loss of blood supply. Other types of arthritis are caused by trauma to the joint while others, such as rheumatoid arthritis, Lupus, and psoriatic arthritis destroy cartilage and are associated with the inflammation of the joint lining.

The hip joint is one of the joints that is commonly afflicted with arthropathy. The hip joint is a ball and socket joint that joins the femur or thighbone with the pelvis. The pelvis has a semispherical socket called the acetabulum for receiving a ball socket head in the femur. Both the head of the femur and the acetabulum are coated with cartilage for allowing the femur to move easily within the pelvis. Other joints commonly afflicted with arthropathy include the spine, knee, shoulder, carpals, metacarpals, and phalanges of the hand.

Arthroplasty as opposed to arthropathy commonly refers to the making of an artificial joint. In severe cases of arthritis or other forms of arthropathy, such as when pain is overwhelming or when a joint has a limited range of mobility, a partial or total replacement of the joint within an artificial joint may be justified. The procedure for replacing the joint varies, of course, with the particular joint in question, but in general involves replacing a terminal portion of an afflicted bone with a prosthetic implant and inserting a member to serve as a substitute for the cartilage.

The prosthetic implant is formed of a rigid material that becomes bonded with the bone and provides strength and rigidity to the joint and the cartilage substitute members chosen to provide lubrication to the joint and to absorb some of the compressive forces. Suitable materials for the implant include metals and composite materials such as titanium, cobalt chromium, stainless steel, ceramic and suitable materials for cartilage substitutes include polyethylene, ceramics, and metals. A cement may also be used to secure the prosthetic implant to the host bone.

A total hip replacement, for example, involves removing the ball shaped head of the femur and inserting a stem implant into the center of the bone, which is referred to as the medullary canal, or marrow of the bone. The stem implant may be cemented into the medullary canal or may have a porous coated surface for allowing the bone to heal directly to the implant. The stem implant has a neck and a ball shaped head, which are intended to perform the same functions as a healthy femur's neck and a ball shaped head. The polyethylene cup is inserted into the acetabulum and has a socket for receiving the head on the stem implant.

The polyethylene cup may be positioned directly into the acetabulum. Preferably, the polyethylene cup is secured to a metal member, which is in turn secured to the acetabulum. This metal member is typically called a cup or a shell. The cup or shell may include a porous coating for promoting bony in-growth to secure the shell to the acetabulum. Alternatively or in addition the shell may include an opening or a plurality of openings for receiving bone screws to assist in the attachment of the shell to the acetabulum. As an alternative to the polyethylene cup, a cup of a different material may be inserted into the shell. For example, the cup may be made of a metal, for example, cobalt chromium, stainless steel, or titanium. Alternatively, the cup may be made of a ceramic.

More recently, the polyethelene cup as a hip cup prosthesis has been replaced with a more rigid component. For example, in more recent hip cup prostheses, the cup is made of, for example, a metal or a ceramic. The head may be made of a metal or a ceramic. For example, the cup may be made of a ceramic and the head may likewise be made of a ceramic. Alternatively, the cup may be made of a metal and the head may likewise be made of that similar metal. It should be appreciated that a ceramic cup may be utilized with a metal head and a metal cup may be utilized with a ceramic head.

To maximize the life of the prosthesis, the accuracy of the dimensional characteristics of the components of the prosthesis as well as the surface condition, for example the surface finish, is extremely critical in the life of the prosthesis.

Dimensional errors and surface finish imperfections may cause the prosthesis to prematurely wear. The components that wear on the prosthesis, particularly those that wear rapidly, may lead to reactions with the tissues of the body. Such reaction to foreign objects is called osteolysis. Osteolysis can damage soft tissue and further complicate the replacement of the prosthesis.

Attempts have been made to provide for improved finishes and geometries of the articulating surface of a prosthesis. For example, the surfaces may be polished by hand by, for example, a rubbing compound or by a metal or cloth buffing wheel. Alternatively, the surfaces may be smoothed by robotic manipulators using similar tools as are used by hand. Alternatively, the components have the articulating surface of the prosthesis may be polished by a finishing device, for example a RotoFinish® tumbling machine. These prior art attempts at providing improved geometry and finish to the articulating surface of a prosthetic component are slow and inaccurate. Further, the use of the continual attempts to improve the finish on the part may affect its geometry or shape. Imperfections in shape and or finish may greatly reduce the operating life of the prosthesis and may lead to osteolysis.

The present invention is adapted to solve at least some of the aforementioned problems with the prior art.

SUMMARY OF THE INVENTION

This invention is directed to improved devices and methods for polishing orthopaedic implant components in a Magnetorheological Polishing fluid (hereinafter referred to as "MP-fluid"). More particularly, this invention is directed to a highly accurate method of polishing implant components in a MP-fluid that may be automatically controlled and may improve polishing devices.

These fluids are of at least two types. The first type of fluids are mixtures of abrasive particles and magnetic particles. The abrasive particles are in suspension and magnetic particles are in suspension in a fluid. The magnetic particles are coated with Teflon®, a trademark of E. I. DuPont de Nemours and Company, to protect them from degradation. These particles could be suspended in solutions of glycerin, glycol, water, oil, alcohol, or mixtures thereof. When a magnetic field is applied, the magnetic particles create a plastic zone, and the abrasive particle provide for polishing action.

The first type of fluids are used in manufacturing equipment that utilizes the MP-fluid finishing process is commercially available from QED Technology, Inc., Rochester, N.Y. and sold as the Q-22MRF System.

The second type of fluid includes a finer sized particle having a combination of magnetic and abrasive properties. The particles are, for example iron (Fe) metal nanoparticles that are coated with SiC. The particles may, alternatively, be, for example, cobalt (Co), samarium (Sm), neodymium (Nd), erbium (Eb), copper (Cu), nickel (Ni), or silver (Ag). The particles should be magnetic. Silicon carbide (SiC) is a hard functional material and has good thermal conductivity. Coating the metal nanopowder with SiC can prevent oxidation of the metal nanopowder and improve the dispersion and mechanical property of the nanopowder. These particles also could be suspended in solutions of glycerin, glycol, water, oil, alcohol, or mixtures thereof.

A research group headed by Joseph Lik Hang Chau at the Ultrafine Powders Laboratory, Materials Research Laboratories, Industrial Technology Research Institute, Taiwan, has produced such second type of particles. A Lexis Nexis article entitled "MICROWAVE PLASMA SYNTHESIS OF ENCAPSULATED METAL NANOPOWDERS" available on the Lexis Nexis website further describes the activities of Mr. Chau and is summarized herein below.

When mentioning MP fluids herein it will be understood to mean the alternative use of either the type one fluids or the type two fluids mentioned above.

The method of this invention comprises the steps of creating a polishing zone within a MP-fluid; bringing an implant component to be polished into contact with the polishing zone of the fluid; determining the rate of removal of material from the surface of the object to be polished; calculating the operating parameters, such as magnetic field intensity, dwell time, and spindle velocity for optimal polishing efficiency; and moving at least one of said object and said fluid with respect to the other according to the operating parameters.

The polishing device includes an object to be polished; and a MP-fluid, which may or may not be contained within a vessel. The device also includes means for inducing a magnetic field, and mean for moving one or more of these components with respect to one or more of the other components. The orthopaedic component or object to be polished is brought into contact with the MP-fluid, and the MP-fluid, the means for inducing a magnetic field, and/or the object to be polished are put into motion, thereby allowing all facets of the object to be exposed to the MP-fluid.

In the method and devices of this invention, the MP-fluid is acted upon by a magnetic field in the region where the fluid contacts the object to be polished. The magnetic field causes the MP-fluid to acquire the characteristics of a plasticized solid whose yield point depends on the magnetic field intensity and the viscosity. The yield point of the fluid is high enough that it forms an effective polishing surface, yet still permits movement of abrasive particles. The effective viscosity and elasticity of the MP-fluid when acted upon by the magnetic field provides resistance to the abrasive particles such that the particles have sufficient force to abrade the work piece.

This invention is directed to improve devices and methods for polishing orthopaedic articulating surfaces MP-fluid. More particularly, this invention is directed to a highly accurate method of polishing the articulating surfaces of orthopaedic joint implant components in a MP-fluid, which, may be automatically controlled, and to improve polishing devices.

The method of this invention includes the steps creating the polishing zone within a MP-fluid, bringing objects into contact with the polishing zone of the fluid, determining the rate of removal of material from the surface of the object to be polished, controlling the operating parameters, such as magnetic field intensity, cycle time and spindle velocity for polishing efficiency, and translating at least one of the object and the fluid with respect to each other according to the operating parameters.

The polishing device includes an orthopaedic component or object to be polished, a MP-fluid, which may or may not be contained within a vessel, means for inducing a magnetic field, and means for moving at least one of these components in respect to the other or more of the other components. The object to be polished is brought into contact with the MP-fluid and the unique MP-fluid together with means for inducing a magnetic field, and/or the object to be polished are put into motion, thereby allowing all facets of the object to be exposed to the MP-fluid.

In the method and devices for this invention, the MP-fluid is reacted upon by a magnetic field in the region where the fluid contacts the object to be polished. The magnetic field causes the MP-fluid to acquire the characteristics of a plasticized solid whose yield point depends on the magnetic field intensity and the viscosity. The yield point of the fluid is high enough that it forms an effective polishing surface, yet still permits movement of abrasive particles. The effective viscosity and elasticity of the MP-fluid when acted upon by the magnetic field, provides assistance to the abrasive particles such that the particles have sufficient force to abrade the work piece.

The process of the present invention is best understood by thinking of the MP-fluid as a compliant replacement for a conventional sub-aperture polishing lap. The fluid's viscosity is magnetically manipulated while in contact with the working surface to create a sub-aperture polishing lap that conforms to the surface. The process of the current invention has distinctive values that eliminate the problems of classical polishing.

The fluid characterizes and operates the polishing tool. The polishing tool adapts to complex shapes because of this compliant fluid. The process removal rates are very high resulting in short process times.

A small quantity of MP-fluid is loaded into the vessel, for example, a closed-loop fluid delivery system wherein fluid properties such as, for example, temperature and viscosity, are continually monitored and controlled. The fluid is drawn out of the conditioner and extruded onto a, for example, rotating spherical wheel, in a thin ribbon that will contact the articulating surface of the prostheses. The ribbon is then moved via suction and fed back into the conditioner.

An electromagnet, located, for example, below the, polishing wheel, has specifically designed pole pieces that extend up to the underside of the apex of the wheel rim. The pole pieces exert a strong local magnetic field gradient over the upper side of the wheel. When the MP-fluid passes through the magnetic field, it stiffens in milliseconds, and then returns to its original fluid state as it leaves the field again in milliseconds.

This precisely controlled zone of magnetized fluid becomes the polishing tool when an articulating surface is placed into the fluid in the zone. The stiffened fluid ribbon is squeezed from its original thickness of about two (2) millimeters to about one (1) millimeter. The squeezing results in significant sheer stress at subsequent polishing pressure over that section of the articulating surface of the orthopaedic implant. At the same instance the MP-fluid conforms to the local curvature of the articulating surface being polished.

Manufacturing equipment that utilizes the MP-fluid finishing process is commercially available from QED Technology, Inc., Rochester, N.Y. and sold as the Q-22MRF System. The use of such equipment to polish surfaces is more fully described in U.S. Pat. Nos. 5,449,313 and 5,577,948 assigned to Byelocorp Scientific Inc., Rochester, N.Y., and hereby incorporated by reference in its entireties.

According to an aspect of the present invention, a system for use in preparing an articulating surface of a component of an orthopaedic implant is provided. The system includes a magnetorheological polishing fluid including a carrier fluid and a plurality of particles suspendable in said carrier fluid. The system also includes a vessel for containing the magnetorheological polishing fluid. The system also includes a mechanism for delivering the fluid to form a polishing zone and a holder for securing the component and for moveably positioning the articulating surface of the component relative to the polishing zone. The system further includes a controller for determining the rate of material removal from the object, for determining the direction and velocity of movement of the polishing zone relative to the object and for determining the number of cycles of polishing required.

These fluids are of at least two types. The first type of fluids are mixtures of abrasive particles and magnetic particles. The abrasive particles are in suspension and magnetic particles are in suspension in a fluid. The magnetic particles are coated with Teflon®. These particles could be suspended in solutions of glycerin, glycol, water, oil, alcohol, or mixtures thereof. When a magnetic field is applied, the magnetic particles create a plastic zone, and the abrasive particle provide for polishing action. The second type of fluid includes a finer sized particle having a combination of magnetic and abrasive properties. The particles are, for example iron (Fe) metal nanoparticles that are coated with SiC. These particles also could be suspended in solutions of glycerin, glycol, water, oil, alcohol, or mixtures thereof.

In another aspect, the present invention provides a method of preparing a component of a prosthetic implant for use in orthopaedic surgery. The method includes the steps of creating a polishing zone within a Magnetorheological polishing fluid and controlling the consistency of the fluid in the polishing zone. The method includes the steps of bringing the object into contact with the polishing zone of the fluid and causing the object and the polishing zone to move with respect to each other. The method further includes the steps of determining the rate of material removal for the object and determining the direction and velocity of movement of the polishing zone relative to the object. The method includes the step of determining the number of cycles of polishing required.

In another aspect of this method, the step of determining the rate of material removal for the object includes determining the spatial distribution of material removal.

In another aspect of this method, the movement of the polishing zone relative to the object is continuous.

In another aspect of this method, the step of determining the direction and velocity of movement of the polishing zone relative to the object includes determining the size of a contact section of the object in contact with the polishing zone at any given time, determining the thickness of the material layer to be removed during one cycle of polishing, and determining the velocity of the polishing zone.

In another aspect of this method, the movement of the polishing zone relative to the object is in discrete steps.

In another aspect of this method, the step of determining the direction and velocity of movement of the polishing zone relative to the object include determining the size of a contact section of the object in contact with the polishing zone at any given time, determining the displacement of the polishing zone in a single step, determining the coefficient of overlapping, determining the thickness of the material layer to be removed during one cycle of polishing, determining the dwell time for each step of polishing, and determining the number of steps required.

In another aspect of this method, the steps further include displacing the object from its vertical axis to an angle.

In another aspect of this method, the object is displaced from its vertical axis to an angle at a continuous velocity.

In another aspect of this method, the step of displacing the object from its vertical axis to an angle at a continuous velocity further includes determining the angle dimension of the contact spot, determining the thickness of the material layer to be removed during one cycle of polishing, and determining the angular velocity of the displacement of the object to an angle.

In another aspect of this method, the object is displaced from its vertical axis to an angle in discrete steps.

In another aspect of this method, the step of displacing the object from its vertical axis to an angle in discrete steps further includes determining the angle dimension of the contact spot, determining the thickness of the material layer to be removed during one cycle of polishing, determining the value of the angle displacement of a single step, determining the coefficient of-overlapping, and determining the dwell time at each step.

In another aspect of this method, the magnetorheological polishing fluid includes magnetic particles coated with abrasive particles.

In another aspect of this method, the step of controlling the properties of the magnetorheological polishing fluid includes replenishing the carrying fluid during polishing.

In another aspect of this method, the magnetorheological polishing fluid includes a combination of abrasive particles and magnetic particles.

In another aspect of this method, the magnetorheological polishing fluid is contained within a vessel having a reference surface.

In another aspect of this method, the vessel is moved relative to the object.

In another aspect of this method, the vessel is rotated at specified velocities.

In another aspect of this method, the polishing zone is nominally one third of the surface area of the object or less.

In another aspect of this method, the step of creating a polishing zone within a magnetorheological polishing fluid includes the steps of inducing a magnetic field in the vicinity of the magnetorheological polishing fluid, and controlling the direction and intensity of the magnetic field.

In another aspect of this method, the step of controlling the polishing of the object is accomplished by controlling the magnetic field intensity and the location of the polishing zone relative to the surface of the object.

In another aspect of this method, the step of polishing is controlled by a programmable control unit.

In another aspect of this method, the magnetic field is created by a means for inducing a magnetic field which is located outside of the vessel.

In another aspect of this method, the step of creating a polishing zone within a magnetorheological polishing fluid includes subjecting the Magnetorheological polishing fluid to a non-uniform magnetic field, having magnetic field lines that are perpendicular to the gradient of said field, in a region adjacent to the object.

In another aspect of this method, the gradient of the magnetic field is directed toward the bottom of the vessel reference surface.

In another aspect of this method, the method further includes the step of determining the clearance between the object and the vessel reference surface.

In another aspect of this method, the magnetorheological polishing fluid is used to polish abrasive material therein.

In another aspect, the present invention provides a machine for preparing a surface of a component of a prosthetic implant for use in orthopaedic surgery. The machine includes a magnetorheological polishing fluid including a carrier fluid and a plurality of particles suspendable in the carrier fluid. The machine also includes a frame and a vessel for storing the Magnetorheological polishing fluid. The vessel is operatively connected to the frame. The machine also includes a means for subjecting the Magnetorheological polishing fluid to the surface of the component. The means for subjecting the Magnetorheological polishing fluid to the surface of the component is operatively connected to the frame. The machine further includes a means for creating relative motion between the Magnetorheological polishing fluid and the surface of the component. The means for creating relative motion is operatively connected to the frame.

In another aspect of the machine of the present invention, the vessel is adapted for receiving the component and for submersing at least a portion of said component in magnetorheological polishing fluid.

In another aspect of the machine of the present invention, the device for subjecting the magnetorheological polishing fluid to the surface of the component includes a pump operatively connected to the vessel for applying the magnetorheological polishing fluid to the surface of the component.

In another aspect of the machine of the present invention, the device for creating relative motion between the magnetorheological polishing fluid and the surface of the component includes rotating the component relative to the magnetorheological polishing fluid.

In another aspect of the machine of the present invention, the device for creating relative motion between the magnetorheological polishing fluid and the surface of the component includes means for flowing the magnetorheological polishing fluid on the surface of the component.

In another aspect of the machine of the present invention, the means for flowing the magnetorheological polishing fluid on the surface of the component includes a pump.

In another aspect of the machine of the present invention, the machine further includes a surface finish-measuring device. The surface finish measuring device is operatively connected to the frame for providing a measurement of the surface finish of the articulating surface of the component.

In another aspect of the machine of the present invention, the surface finish measuring device uses optics to measure the surface finish of the articulating surface of the component.

In another aspect of the machine of the present invention, the surface finish measuring device uses electrical conductivity to measure the surface finish of the articulating surface of the metal component.

In another aspect of the machine of the present invention, the machine further includes a magnetic field generating device. The magnetic field generating device is operatively connected to the frame for exposing the articulating surface of the metal component to a magnetic field to alter the metal removing characteristics of the machine.

In another aspect of the machine of the present invention, the magnetic field generating device provides an adjustable magnetic field.

In another aspect of the machine of the present invention, the machine further includes a heater operatively connected to the frame. The heater for elevating the temperature of the articulating surface of the component to alter the material removing characteristics of the system.

In another aspect of the machine of the present invention, the machine further includes a particle measuring device operatively connected to the frame. The particle measuring device measures the content of particles in the magnetorheological polishing fluid.

In another aspect of the machine of the present invention, the particle measuring device includes a light emitting device for emitting light onto the magnetorheological polishing fluid.

In another aspect of the machine of the present invention, the particle measuring device further includes a meter for measuring the light reflected from the magnetorheological polishing fluid.

In another aspect of the machine of the present invention, the particle measuring device measures at least one of the turbidity, the absorption and the reflectance of the magnetorheological polishing fluid.

In another aspect of the machine of the present invention, the particle measuring device measures the electrical conductivity of the magnetorheological polishing fluid.

In another aspect of the machine of the present invention, the magnetorheological polishing fluid includes magnetic particles coated with abrasive particles.

In another aspect of the machine of the present invention, the Magnetorheological polishing fluid includes a combination of abrasive particles and magnetic particles.

In another aspect of the machine of the present invention, the surface finish measuring device uses interferometry to measure the surface finish of the articulating surface of the component.

In yet another aspect of the present invention a method of preparing a component of a prosthetic implant for use in orthopaedic surgery is provided. The method includes the steps of, creating a polishing zone within a Magnetorheological polishing fluid, controlling the consistency of the fluid in the polishing zone, bringing the object into contact with the polishing zone of the fluids, and causing the object and the polishing zone to move with respect to each other.

In another aspect, the present invention provides a fixture for securing an orthopaedic implant to a machine while applying a Magnetorheological polishing fluid to the articulating surface of the implant. The fixture includes a body, means to secure the body to the machine, and means to secure the implant to the body.

The technical advantages of the present invention include the ability to provide quicker polishing time and less labor in providing surface finishes to the articulating surface of orthopaedic prosthesis. For example, according to one aspect of the present invention, a process is provided to polish the articulating surface of an orthopaedic implant with a MP-fluid. The fluid is acted upon by a magnetic field in the region where the fluid contacts the object to be polished. The field causes the fluid to acquire characteristics of a plasticized solid whose yield point depends on the field intensity and the viscosity. The yield point of the fluid is high enough that the fluid forms an effective polishing surface while still permitting movement of abrasive particles. Thus, the present invention provides for quicker polish times and less labor to polish an articulating surface of an orthopaedic implant.

The technical advantages of the present invention include the ability to lower surface finishes while improving geometrical dimensions on the articulating surface of an orthopaedic implant. For example, according to another aspect of the present invention, a machine is provided that utilizes a MP-fluid that is acted upon by a magnetic field in the region where the fluid contacts the object to be polished. The field causes the fluid to acquire the characteristics of a plasticized solid. The yield point of the fluid is high enough to permit effective polishing of the surfaces. The work piece is held and the polishing intensity is distributed along the articulating surfaces of the prosthesis such that the surface finish may be improved while also potentially improving the geometry of the articulating surface. Thus, the present invention provides for improved accuracy of the dimensioning of the articulating surface of the orthopaedic implant.

The technical advantages of the present invention include the ability to lower surface finish while improving geometrical dimensions on the articulating surface of an orthopaedic implant. For example, according to another aspect of the present invention, a machine is provided that utilizes a MP-fluid that is acted upon by a magnetic field in the region where the fluid contacts the object to be polished. The field causes the fluid to acquire the characteristics of a plasticized solid. The yield point of the fluid is high enough to permit effective polishing of the surfaces. The work piece is held and the polishing intensity is distributed along the articulating surfaces of the prosthesis such that the geometry of the articulating surface is improved while also lowering the surface finish. The improved form or geometry may be achieved by taking measurements of the implant, i.e. interferometric data, and feeding this information into the controller so that the magnetic field is applied only to the "high" spots that need reduction to achieve perfect form. Thus, the present invention provides for improved accuracy of the dimensioning of the articulating surface of the orthopaedic implant.

The technical advantages of the present invention further include the ability to reduce orthopaedic implant wear, lengthen orthopaedic implant life, and lessen the incidence and effects of osteolysis. For example, according to another aspect of the present invention, a method is provided for improving the surface finish of the articulating surface of an orthopaedic implant such that the wear to the articulating surface of the implant is reduced, thus lengthening implant life and reducing osteolysis occurrence. The MP-fluid is acted upon by a magnetic field in the region where the fluid contacts the object to be polished. The effective viscosity and elasticity of the fluid when acting upon the orthopaedic component provides resistance to abrasive particles such as a particle to abrade the work piece. Thus the present invention provides for improved surface finish and a longer orthopaedic implant life.

The technical advantages of the present invention include the ability to provide longer life and less wear on the orthopaedic implant. For example, according to another aspect of the present invention, a method is provided for polishing an orthopaedic implant-articulating surface. The process includes the steps of presenting the orthopaedic implant articulating surface to a flow of MP-fluid which acts upon the surface and provides resistance to the abrasive particles such that the particles have sufficient force to abrade the work piece and smooth the surfaces. Thus the present invention provides for longer life and less wear on the orthopaedic implant-articulating surface.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which.

Corresponding reference characters indicate corresponding parts throughout the several views. Like reference characters tend to indicate like parts throughout the several views.

DETAILED DESCRIPTION OF THE PREFERRED EMBODIMENTS

Embodiments of the present invention and the advantages thereof are best understood by referring to the following descriptions and drawings, wherein like numerals are used for like and corresponding parts of the drawings.

Figure 1:
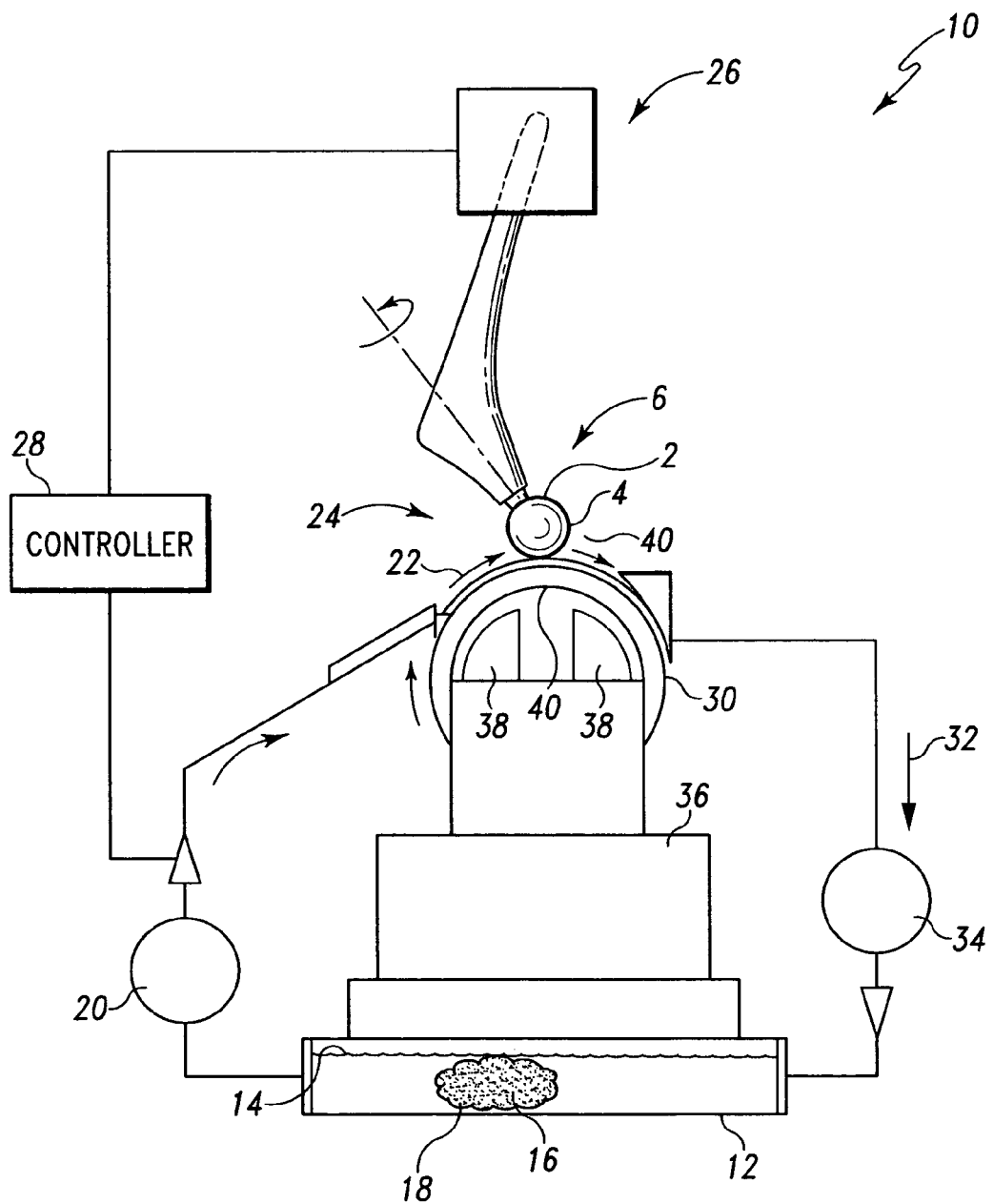
FIG. 1 is a schematic drawing of a polishing device for use with an embodiment of the present invention.
Figure 10:
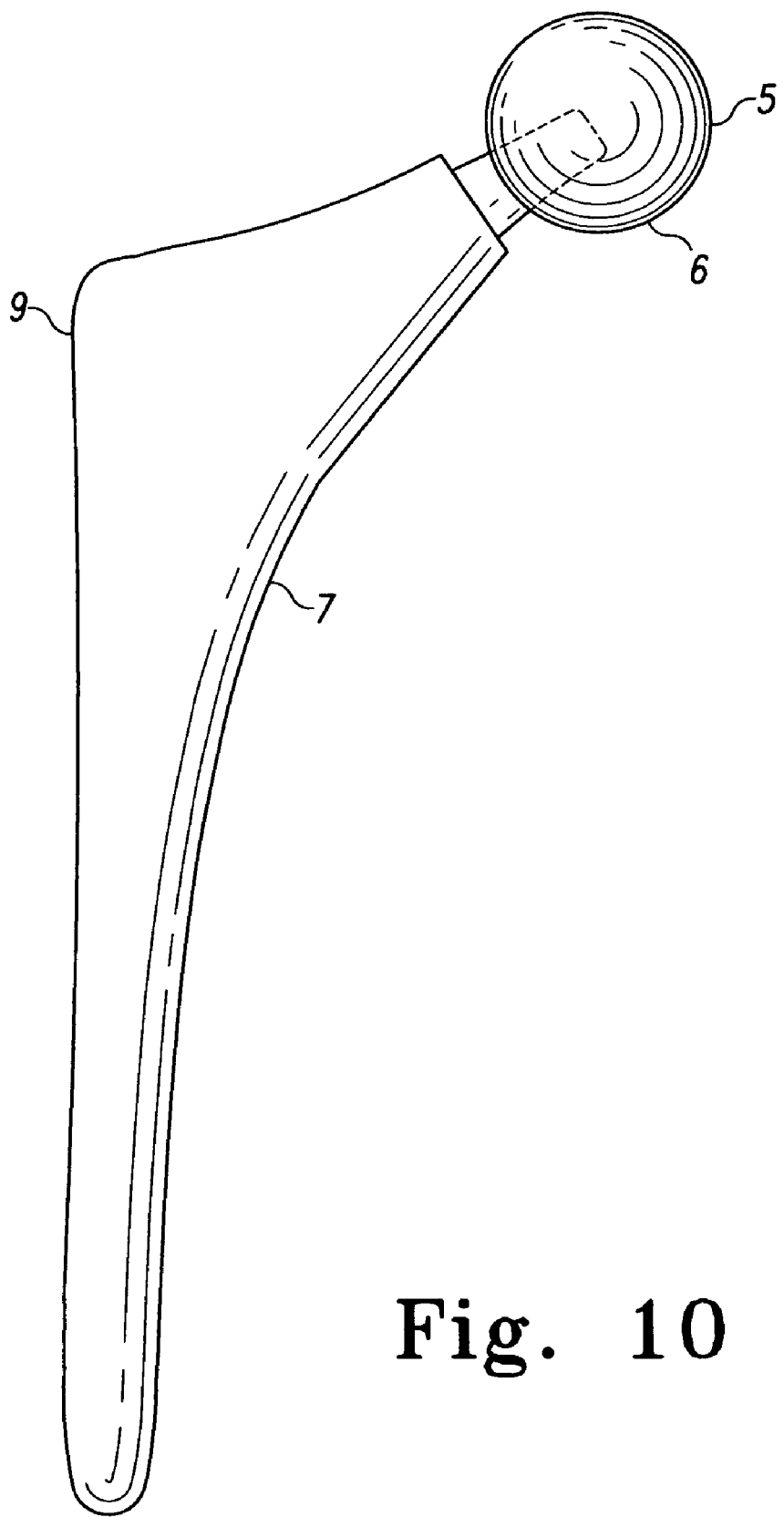
FIG. 10 is a plan view of a hip stem for use with the polishing device of an embodiment of the present invention.

According to the present invention and referring to FIG. 1, an embodiment of the present invention is shown as system 10. System 10 is utilized for preparing an articulating surface 2 of a component 4 of an orthopaedic implant 6. The articulating surface 2 may, as shown in FIG. 1, be a convex surface, for example a portion of the component 4. The component 4, as shown in FIG. 10, may be in the form of an orthopaedic hip implant head. The orthopaedic implant 6 may, as shown in FIG. 1, be in the form of a hip prosthesis. It should be appreciated that the orthopaedic implant 6 may, alternatively, be any orthopaedic joint component. Components with flat or convex peripheries, such as knee femoral components, hip heads, hip stem components, tibial trays, and humeral heads are particularly well suited for use with the system 10.

The system 10, as shown in FIG. 1, includes a vessel 12 for containing a fluid 14. The vessel 12 may be any vessel capable of containing a fluid, for example fluid 14. The vessel 12 may, as shown in FIG. 1, be used strictly as a reservoir to maintain and contain a portion of the fluid 14 or may, as shown later, be utilized to submerse a portion of the implant or work piece for polishing.

The fluid 14 may, as shown in FIG. 1, include a magnetic particle 16, which is suspendable in the fluid 14 to form a MP-fluid 18.

Composition of the MP-fluid 18 may be any fluid capable of performing within the aspects of the present invention. The MP-fluid is preferably as described in U.S. Pat. No. 5,449,313 incorporated herein in its entirety by reference. U.S. Pat. No. 5,577,948 is also incorporated in its entirety herein by reference.

MP fluids 18 are of at least two types. The first type of fluids is mixtures of abrasive particles and magnetic particles. The abrasive particles are in suspension and magnetic particles are in suspension in a fluid. The magnetic particles are coated with Teflon®, a trademark of E. I. DuPont de Nemours and Company, to protect them from degradation. These particles could be suspended in solutions of glycerin, glycol, water, oil, alcohol, or mixtures thereof. When a magnetic field is applied, the magnetic particles create a plastic zone, and the abrasive particles provide for polishing action.

The first type of fluids are used in manufacturing equipment that utilizes the MP-fluid finishing process is commercially available from QED Technology, Inc., Rochester, N.Y. and sold as the Q-22MRF System.

In an embodiment of the present invention, the fluid comprises a plurality of magnetic particles, a stabilizer, and a carrying fluid selected from the group consisting of water and glycerine. In another embodiment, the magnetic particles 16, (preferably carbonyl iron particles), are coated with a protective layer of a polymer material which inhibits their oxidation. The protective layer is preferably resistant to mechanical stress as much as is practical. In another preferred embodiment, using the coating material polytetrafluoroethylene, PTFE, (commonly known as Teflon®), the particles may be coated by the usual process of micro-capsulization.

Heretofore, the utilization of machines embodying the MP-fluid polishing process have been limited to its use to polish glass and plastic materials. Thus, it should be appreciated that the selection of the MP-fluid previously selected to polish such plastic, glass and ceramic materials may not be as effective for polishing metals. Further, it should be appreciated that the magnetic and thermal conductivity of metals utilized in orthopaedic implants may be quite different than that of the ceramics and glass previously used as the work piece in such equipment.

Due to the oxidizing nature of metals, the polishing media should be selected such that the acidity or pH of the polishing media not be chemically reactive with the metal of the articulating component of the orthopaedic implant to be polished. The pH of the polishing media should be adjusted to more favorably effect the polishing of metals. For example, the pH of the polishing media should be about 6.2 to 7.8 PH. Preferably, the polishing media will be from about 6.8 to 7.2. Appropriate acidic and basic materials may be added to the polishing media to obtain a desired PH for the polishing media.

To accommodate the polishing of the articulating surface of the metal orthopaedic implant, the RE-DOX or oxidation-reduction potential of the polishing media should be adjusted to more favorably effect the polishing of metals. Material may be added to the MP-fluid that will adjust the oxidation-reduction potential of the polishing media. For example, material that will affect the ability of electrons to flow within the polishing media should be adjusted to provide for a polishing media that more favorably effects the polishing of the metals.

When selecting the optimal material for the MP-fluid 18 for the system 10, the particles may be selected to provide for Nano-sized particles. That is, those particles that have a size of less than 50 nanometers for the abrasive media. Such smaller sized nano-particles may provide better finishes for metal substrates. Such nano-sized particles are readily available and can be obtained by proper processing of commercially available particles.

The MP-fluid 18 for the system 10 may be in the form of carbo-nitride particles. Such carbo-nitride particles may be utilized as the abrasive media within the MP-fluid 18. Such carbo-nitride particles may provide for quicker and better finishing of metal surfaces.

As an alternative, the MP-fluid 18 of the system 10 for use to polish articulating surfaces of metallic orthopaedic implants may be in the form of a bonded abrasive magnetic particle system. Such a bonded abrasive magnetic particle system may be in the form of an aluminum oxide, which may be bonded to ferrous oxide using polyfunctional silane molecules, such as trimethoxysilane. Such a bonded abrasive magnetic particle system may provide for improved polishing of metallic surfaces with a MP-fluid.

The second type of fluid includes a finer sized particle having a combination of magnetic and abrasive properties. The particles are, for example iron (Fe) metal nanoparticles that are coated with SiC. The particles may, alternatively, be cobalt (Co), samarium (Sm), neodymium (Nd), erbium (Eb), copper (Cu), nickel (Ni), or silver (Ag). The particles should be magnetic. Silicon carbide (SiC) is a hard functional material and has good thermal conductivity. Coating the metal nanopowder with SiC can prevent oxidation of the metal nanopowder and improve the dispersion and mechanical property of the nanopowder. These particles also could be suspended in solutions of glycerin, glycol, water, oil, alcohol, or mixtures thereof.

The second type of fluid provides for a finer sized particle having a combination of magnetic and abrasive properties, and is expected to provide better finishing results for medical implants without the need for a 2-part MP-fluid. For example one could achieve better uniformity, have a simpler system, and provide a better finish.

A research group headed by Joseph Lik Hang Chau at the Ultrafine Powders Laboratory, Materials Research Laboratories, Industrial Technology Research Institute, Taiwan, has produced such second type of particles. A Lexis Nexis article entitled "MICROWAVE PLASMA SYNTHESIS OF ENCAPSULATED METAL NANOPOWDERS" available on the Lexis Nexis website further describes the activities of Mr. Chau and is summarized as follows.

Magnetic nanoparticles are conventionally prepared be techniques such as solution-phase chemical reduction, thermal decomposition, mechanical attrition. Recently, techniques such as gas-condensation and microwave plasma synthesis have been used. Magnetic nanoparticles owing to their increased surface area have a great affinity to readily react with oxygen, which can result in changes of physical and chemical properties of the nanoparticles. Therefore, encapsulation of these nanoparticles is necessary to prevent further growth, oxidation, and particle agglomeration to retain its original properties. Already, attempts to make this encapsulation have been carried out by polymer stabilization of nanoparticles, silica coatings on metal nanoparticles (iron, copper, nickel).

Silicon carbide (SiC) is a hard functional material and has good thermal conductivity. Coating the metal nanopowder with SiC can prevent oxidation of the metal nanopowder and improve the dispersion and mechanical property of the nanopowder. A research group headed by Joseph Lik Hang Chau at the Ultrafine Powders Laboratory, Materials Research Laboratories, Industrial Technology Research Institute, Taiwan, has developed a two-stage microwave plasma synthesis process to produce cobalt (Co) metal nanoparticles and to finally coat them with SiC. The technique developed is a two-step microwave plasma synthesis process. The fist step involves preparing pure metal nanoparticles. The average size of the core metal nanoparticles can be controlled in the first stage of the synthesis before the coating of the second layer. The SiC is then coated during the second stage immediately after the synthesizing of the pure metal nanopowder.

The microwave plasma unit consisted of a microwave source, resonance chamber, reactor chamber with a quartz tube inside, heat exchanger, and a powder collector. The synthesis was carried out in the reaction region passing a single cavity mode of 2.45 GHz microwave system. Cobalt (II) chloride ($CoCl_2$) was used as the precursor (feed rate of 0.74 g/min) for Co nanopowder synthesis. Whereas, silicon tetrachloride ($SiCl_4$) and hexane ($C_6H_{14}$) were used as precursors for silicon and carbon for the SiC coating on Co nanopowders. The unit has two precursor dosing devices. One of the top doses —$CoCl_2$- which is thermally decomposed by nitrogen plasma and reduced by hydrogen carrier gas, resulting in the formation of Co nanopowders. At a lower position, $SiCl_4$ and hexane are introduced where they decompose to form Si and C. When the as-synthesized Co nanopowders travel down the unit, a thin layer of SiC is formed on the Co nanoparticles. An equal feed rate was maintained for all the precursors employed in the synthesis.

Cobalt nanopowders formed had an average particle size of less than 50 nm. The SiC-coated Co nanoparticles had an average particles size of about 50 nm with a covered shell layer that is approximately 3 nm.

When mentioning MP fluids herein it will be understood to mean the alternative use of either the type one fluids or the type two fluids mentioned above.

Referring again to FIG. 1, the system 10 further includes a device 20 for pumping the fluid 14 in a fluid path 22 to form a polishing zone 24.

The system 10 further includes a holder 26 for securing the implant component 4 and for moveably positioning the articulating surface 2 of the component 4 relative to the polishing zone 24.

The system 10 may further include a controller 28 for determining the rate of material removal from the object for determining the direction and velocity of movement of the polishing zone 24 relative to the implant component 4 and for determining the number of cycles of polishing required. As shown in FIG. 1, the system 10 may be in the form of a closed loop fluid delivery system. The fluid properties, such as temperature and viscosity, may be continually monitored and controlled by the system 10. The fluid 14 may be drawn out of the vessel 12.

The controller 28 may be utilized to improve form or geometry of the implant by taking measurements of the implant, i.e. interferometric data, and feeding this information into the controller 28 so that the magnetic field is applied only to the "high" spots that need reduction to achieve perfect form. The "high" spots may also be placed in the polishing zone 24 for additional time to also achieve the reduction to achieve perfect form.

As shown in FIG. 1, the vessel 12 may be in the form of a MP-fluid conditioner. The conditioner 12 may be utilized to maintain the proper condition of the fluid 18. For the first type of MP-fluid the conditioner 12 may be in the form of a magnetic filter to separate the magnetic particles that have not deteriorated from those that have deteriorated and have lost their magnetic properties. The magnetic particles that have not lost their magnetic properties will be recirculated and those that have lost their magnetic properties will be removed. For the second type of MP-fluid the conditioner may merely measure the properties of the fluid and when the properties fall below a minimum level the MP-fluid may be drained and replaced.

The fluid 18 is drawn out of the vessel 12 and extruded onto, for example and as shown in FIG. 1, a rotating spherical wheel in a thin ribbon that will contact the articulating surface 2 of the implant component 4. The ribbon is then removed by suction and fed back into the conditioner along fluid path 32 and through, as shown in FIG. 1, pump 34.

As shown in FIG. 1, an electromagnet 36 may be located below the spherical polishing wheel 30. The electromagnetic magnet 36 may have specially designed pole pieces 38 that extend up to the underside of the apex 40 of the wheel rim. These pole pieces 38 exert a strong local magnetic field gradient over the upper side of the wheel 30.

When the MP-fluid 18 passes through the magnetic field, it stiffens in milliseconds then returns to its original fluid state as it leaves the field, again in milliseconds. This precisely controlled zone of magnetized fluid becomes the polishing tool. When the articulating surface 2 of an orthopaedic implant component 4 is placed into the fluid 18 in this zone, the stiffened fluid ribbon is squeezed from its original thickness from about 2 millimeters, to about 1 millimeter. The squeezing results in significant sheer stress and subsequent polishing pressure over the section of the articulating surface 2 of the orthopaedic implant 6. At the same instant, the MP-fluid 18 conforms to the local curvature of the implant component 4 being polished.

Figure 1A:
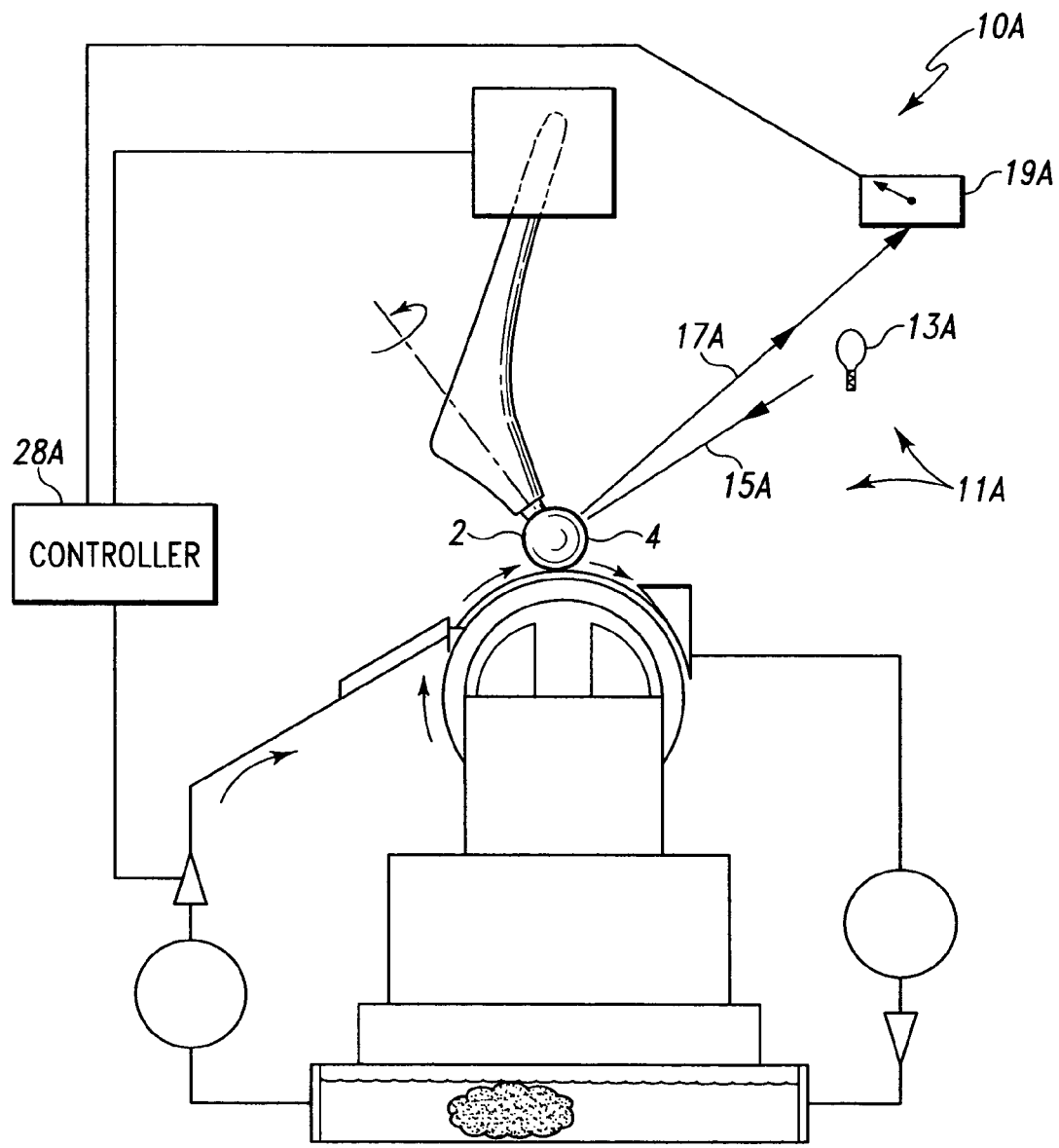
FIG. 1A is a schematic drawing of another polishing device for use with another embodiment of the present invention.

According to the present invention and referring now to FIG. 1A, another embodiment of the present invention is shown as system 10A. System 10A is similar to system 10 of FIG. 1, but additionally includes surface finish feedback control loop 11A. Control loop 11A monitors the surface finish of the articulating surface 2 of the implant component 2 and provides feedback for the controller 28A to control the system 10A. The loop 11A includes a light source 13A in the form of, for example, a laser that is used to direct an incoming beam 15A onto the articulating surface 2 of the implant component 4. The incoming beam 15A from the light source 13A is reflected by the articulating surface 2 of the implant component 4 and is redirected as a reflection beam 17A to a light meter 19A in the form of, for example, an optical processor.

The light meter 19A determines the intensity or strength of the reflected beam 17A. The difference of the intensity of the beam 15A from the light source 13A and the intensity of the beam 17A, which is reflected from the articulating surface 2, measures the reflectivity, which is a measure of the surface finish of the articulating surface 2. The information from the light meter 19A is transmitted to the controller 28A and is used to determine the current surface finish of the articulating surface 2.

Interferometry is a traditional technique in which a pattern of bright and dark lines (fringes) result from an optical path difference between a reference and a sample beam. The incoming light is split inside an interferometer, one beam going to an internal reference surface and the other to the sample. After reflection, the beams recombine inside the interferometer, undergoing constructive and destructive interference and producing the light and dark fringe pattern. A precision translation stage and a CCD camera together generate a 3D interferogram of the object that is stored in the computer memory. This 3D interferogram of the object is then transformed by frequency domain analysis into a quantitative 3D image providing surface structure analysis. Such interferometry systems are available from Zygo Corporation, Middlefield, Conn.

Figure 1B:
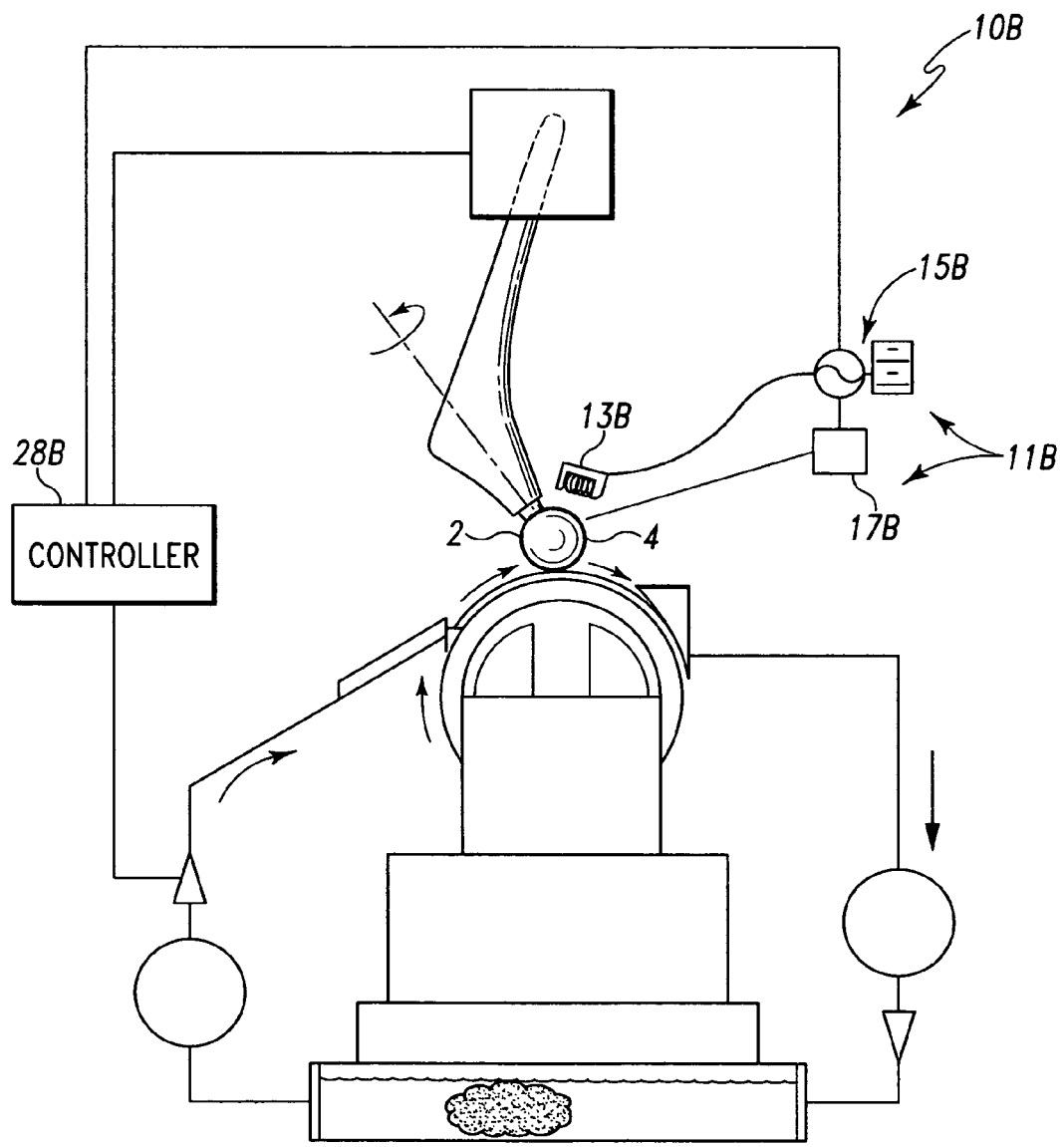
FIG. 1B is a schematic drawing of another polishing device for use with another embodiment of the present invention.

Referring now to FIG. 1B, yet another embodiment of the present invention is shown as system 10B. The system 10B of FIG. 11B is similar to the system 10 of FIG. 1, except that the system 10B includes a control loop 11B for utilizing the magnetic properties of the metallic substrate of the articulating surface 2 of the prosthesis 4 that is polished. Control loop 11B includes, for example, a magnetic generating device, for example an electromagnetic coil 13B, which is positioned adjacent the articulating surface 2 of the prosthesis 4.

The electromagnetic coil 13B is connected to power source 15B as well as to controller 28B. The control loop 11B is used to adjust the magnetic field generated by the electromagnetic coil 13B in response to parameters received by the controller 28B from the surface measuring device 17B in response to the progress of the polishing of the articulating surface 2 of the prosthesis component 4. By utilizing the control loop 11B, the magnetic properties of the metallic substrate of the prosthetic component 4 may be used to influence the polishing process in the system 10B of FIG. 1B.

Figure 1C:
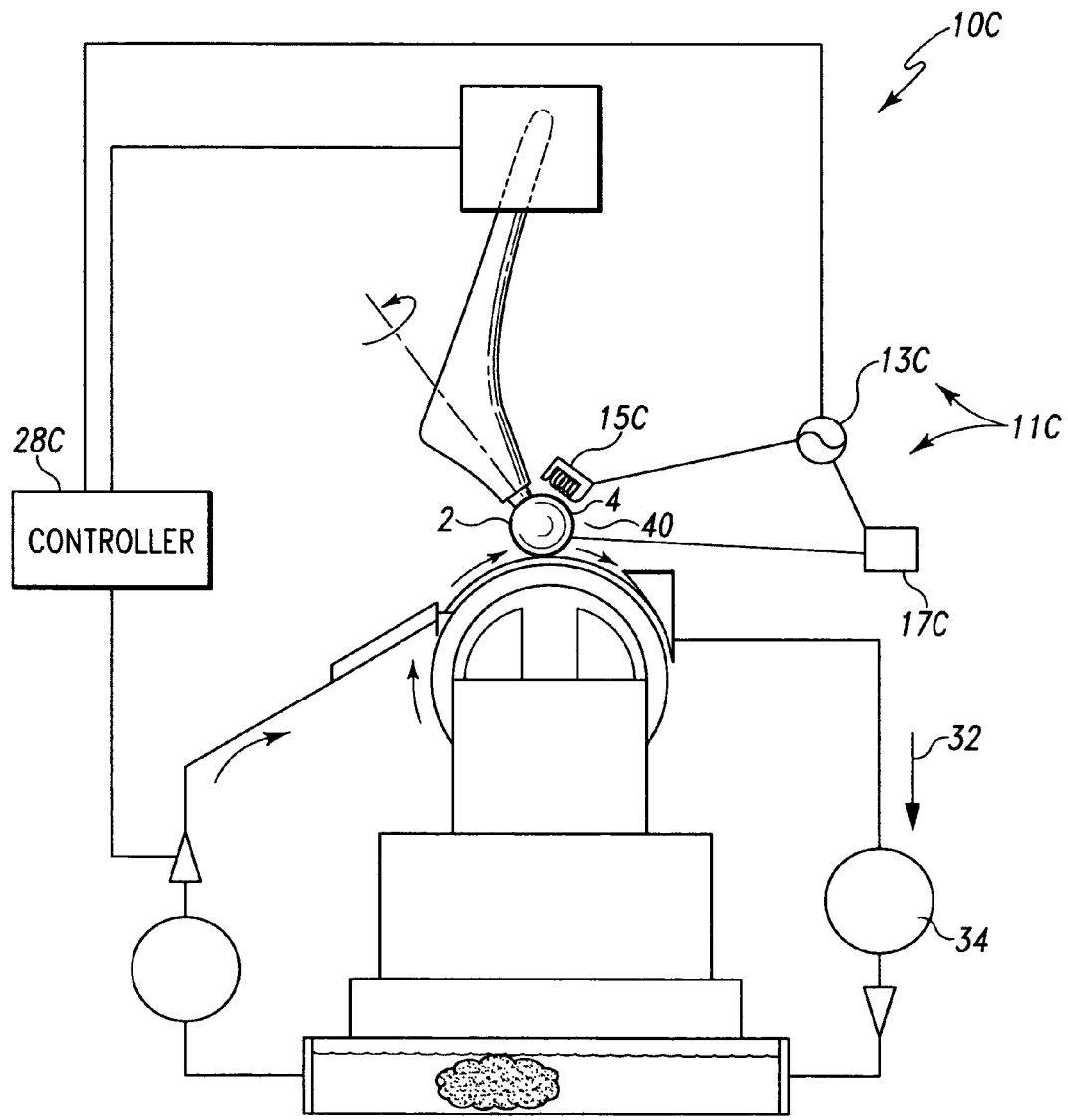
FIG. 1C is a schematic drawing of another polishing device for use with another embodiment of the present invention.

Referring now to FIG. 1C, yet another embodiment of the present invention is shown as system 10C. System 10C is similar to system 10 of FIG. 1, except that system 10C further includes a control loop 11C, which is utilized to utilize the higher thermal conductivity of the metal orthopaedic implant component 4 to heat the substrate of component 4. The localized heating of the articulating surface 2 of the orthopaedic implant 4 will influence the removal rate of material from the surface 2 and thus reduce the polishing time to polish the articulating surface 2 of the prosthetic component 4.

The control loop 11C, as shown in FIG. 1C, may include a power source 13C, which is utilized to heat a warming device, for example induction coil 15C. The induction coil 15C is connected to controller 28C, which is utilized to control the system 10C. The controller 28C takes input from, for example, sensor 17C on surface 2 of prosthesis 4 and send the input to the system 10C to determine the optimum amount of heating of the articulating surface 2 of the prosthesis 4 and thereby turns the induction coil 15C on and off so that the articulating surface 2 of the prosthesis 4 has the ideal temperature to optimize polishing.

Figure 1D:
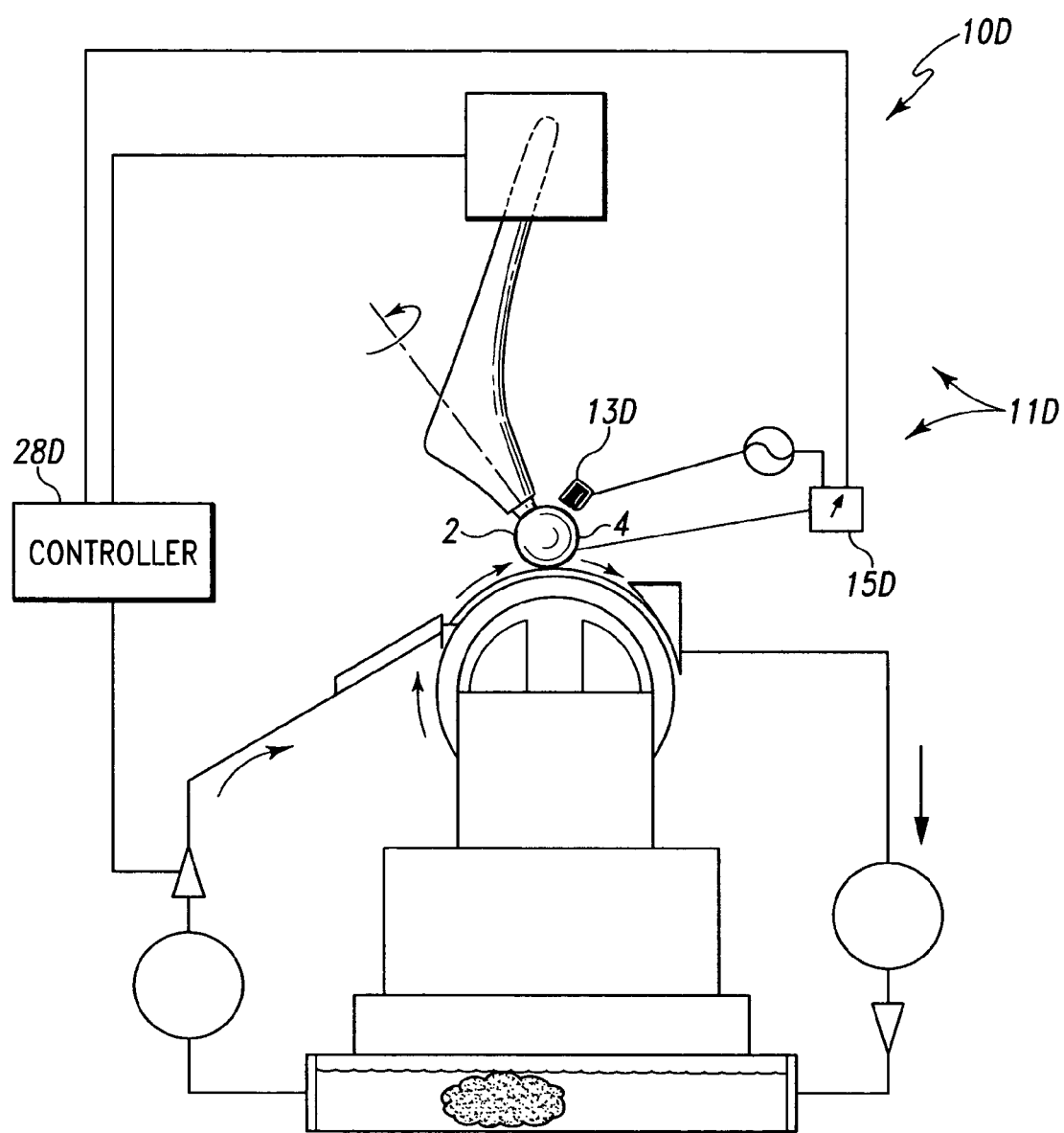
FIG. 1D is a schematic drawing of another polishing device for use with another embodiment of the present invention.

According to the present invention and referring now to FIG. 1D, another embodiment of the present invention is shown as system 10D. The system 10D is similar to the system 10 of FIG. 1, except that the system 10D further includes a control loop 11D, which utilizes the electrical conduction properties of a metallic prosthetic component to be an indicator of the surface finish and polishing progression of the system 10D.

For example, and as shown in FIG. 1D, the system 10D may include the control loop 11D. The control loop 11D may include an electrical contact 13D. While a solitary electrical contact 13D may be sufficient as shown in FIG. 1D, the control loop 11D may also include a plurality of electrical contacts 13D. The electrical contacts 13D may be any type of contact, particularly a contact that may be cooperative with a rotating or moving articulating surface.

For example, as shown in FIG. 1D, the electrical contact 13D may be in the form of brushes. For example, the brushes may be carbon fiber brushes or may be metal brushes. The electrical contacts 13D are connected to a device for measuring electricity, for example a conductivity meter 15D. The conductivity meter 15D is connected to the controller 28D. The measure of the conductivity from the conductivity meter 15D may be used as an indicator of the surface finish of the articulating surface 2 and this feedback may be transferred to the controller 28D to be used in determining the proper processing limits and operations of the system 10D.

Figure 1E:
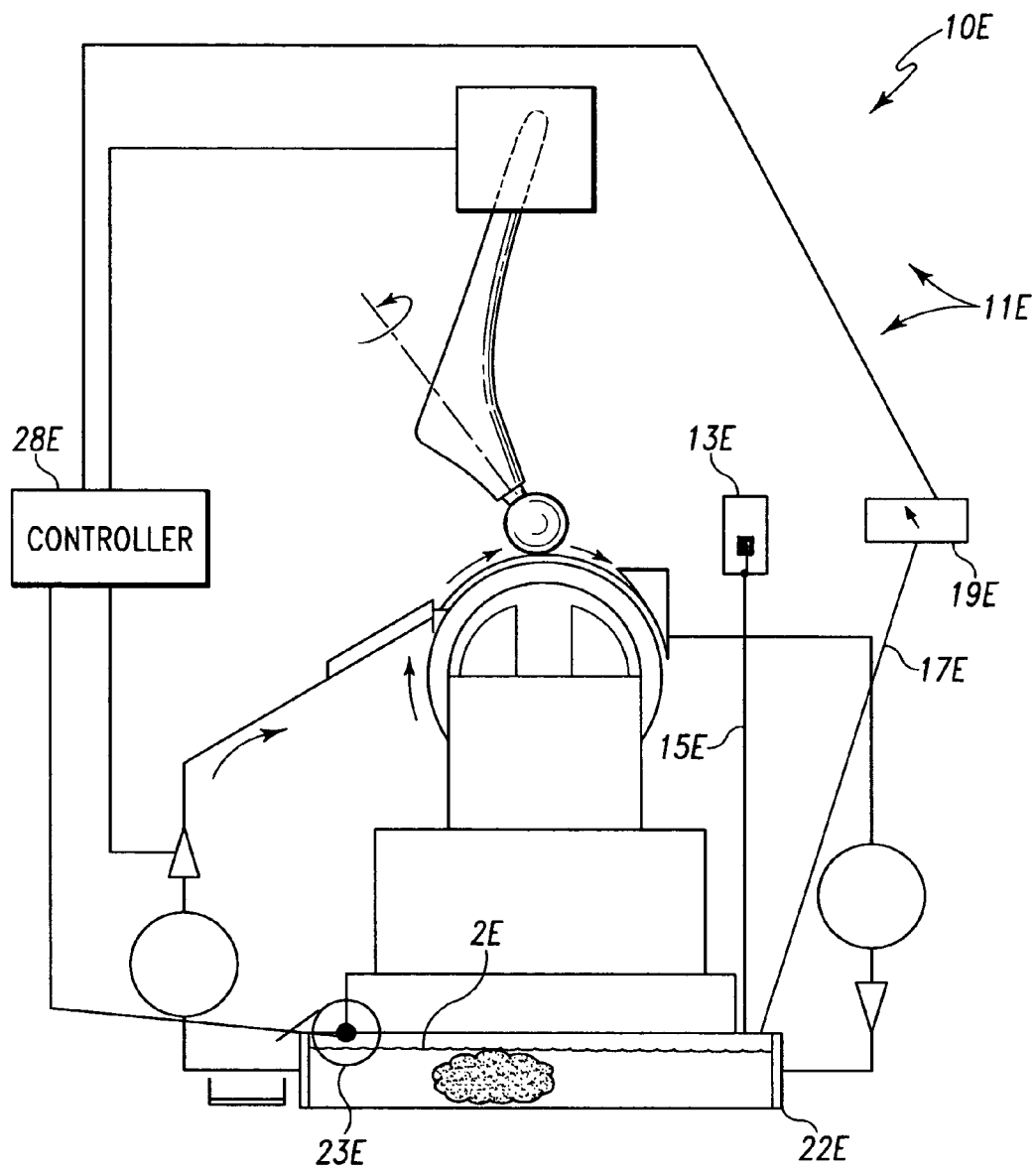
FIG. 1E is a schematic drawing of another polishing device for use with another embodiment of the present invention.

According to the present invention and referring now to FIG. 1E, another embodiment of the present invention is shown as system 10E. System 10E is similar to system 10 of FIG. 1, but additionally includes first polishing fluid particle build-up feedback control loop 11E. Control loop 11E monitors the amount of particles that are suspended in the polishing fluid and provides feedback for the controller 28E to control the system 10E. The first polishing fluid particle build-up feedback control loop 11E utilizes an optical method of measuring the suspended particles.

The loop 11E includes a light source 13E in the form of, for example, a laser that is used to direct an incoming beam 15E onto the surface 2E of the fluid in the vessel 22E. The incoming beam 15E from the light source 13E is reflected by the surface 2 of the fluid in the vessel 22E and is redirected as a reflection beam 17E to a light meter 19E in the form of, for example, an optical processor.

The light meter 19E determines the intensity or strength of the reflected beam 17E. The difference of the intensity of the beam 15E from the light source 13E and the intensity of the beam 17E, which is reflected by the surface 2E of the fluid in the vessel 22E, measures the reflectivity, which is a measure of the suspended content of the fluid in the vessel 22E. The information from the light meter 19E is transmitted to the controller 28E and is used to determine when the fluid has excessive debris content.

It should be appreciated that, alternatively, a system 11E may utilize the light source 13E and a meter 19E to measure either the turbidity or the absorption of the fluid in the vessel 22E. The difference in the intensity of the beam 15E from the light source 13E and the intensity of the beam 17E, which travels through MP-fluid in vessel 22E and through transparent window (not shown), measures the absorption of the MP-fluid in the vessel 22E. The information from light meter 19E is transmitted to controller 28E.

It should be appreciated that to minimize the build-up of metal particles in the vessel 22E, a metal separating filter 23E could be used to constantly remove metal particles from the vessel 22E. The meter 19E and the controller 28E can be used to control the operation of the filter 23E.

For the first type of MP-fluid the metal separating filter 23E may be in the form of a magnetic filter to separate the magnetic particles that have not deteriorated from those that have deteriorated and have lost their magnetic properties. The magnetic particles that have not lost their magnetic properties will be recirculated and those that have lost their magnetic properties will be removed. For the second type of MP-fluid the metal separating filter 23F may be replaced with a device to measure the properties of the fluid and when the properties fall below a minimum level the MP-fluid may be drained and replaced.

Figure 1F:
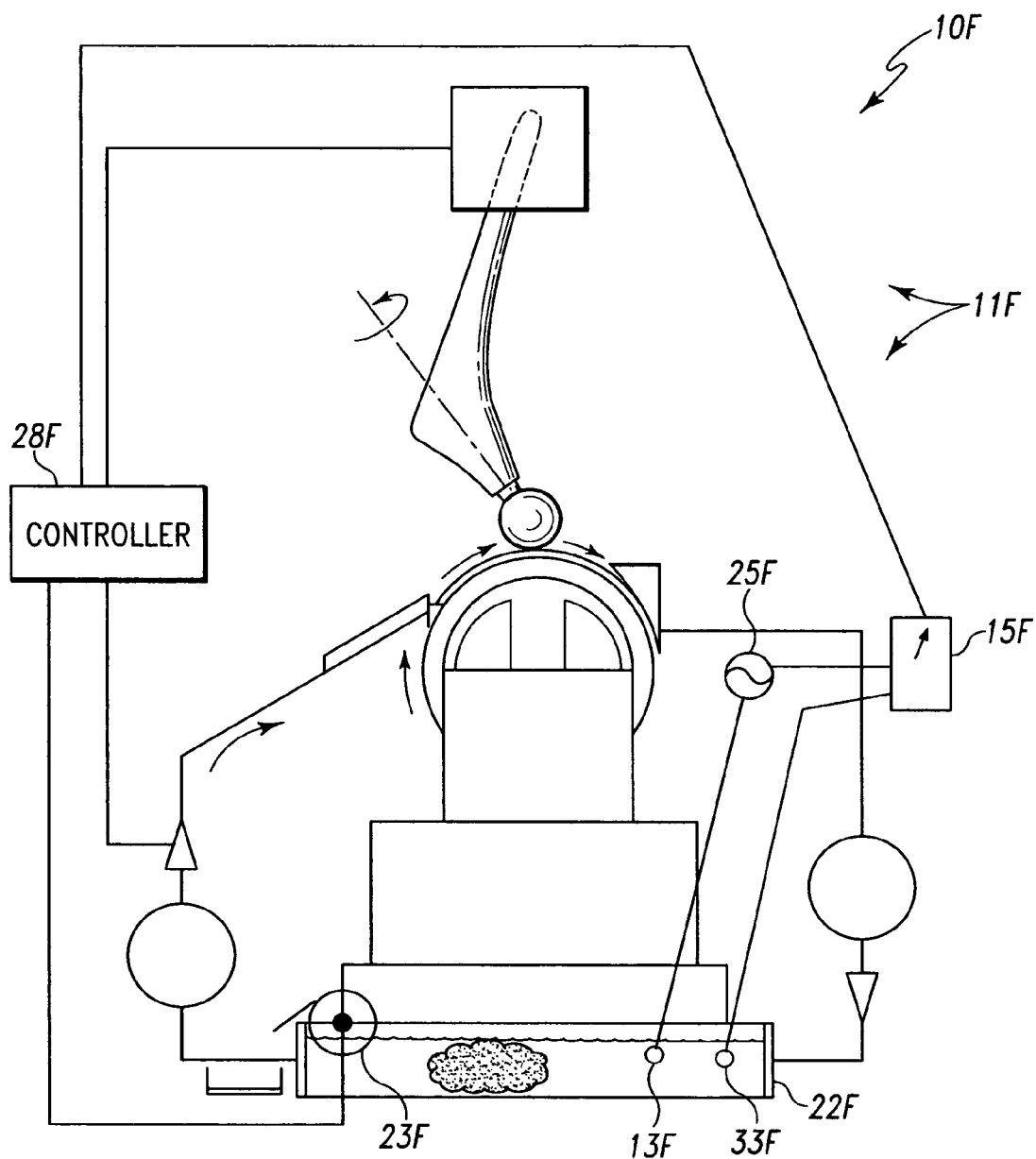
FIG. 1F is a schematic drawing of another polishing device for use with another embodiment of the present invention.

According to the present invention and referring now to FIG. 1F, another embodiment of the present invention is shown as system 10F. System 10F is similar to system 10 of FIG. 1, but additionally includes second polishing fluid metal particle build-up feedback control loop 11F. Control loop 11F monitors the amount of metal particles that are suspended in the polishing fluid and provides feedback for the controller 28F to control the system 10F. The second polishing fluid metal particle build-up feedback control loop 11F utilizes an electrical conductivity method of measuring the suspended metal particles. The Loop measures the electrical conductivity of the fluid in vessel 22F to determine the amount of metal in the fluid in vessel 22F.

For example, and as shown in FIG. 1F, the system 10F may include the control loop 11F that may include first and second electrical contacts 13F and 33F, respectively, suspended in the fluid in the vessel 22F. While a solitary electrical contact 13D or 33F may be sufficient, as shown in FIG. 1F, the control loop 11F may also include a plurality of elements to form the electrical contacts 13F and 33F. The electrical contacts 13F and 33F may be any type of contacts, particularly contacts that may be cooperative with a fluid.

The first electrical contact 13F is connected to an electrical power source 25F. The second electrical contact 33F is connected to a device for measuring electricity, for example a conductivity meter 15F. The conductivity meter 15F is connected to the controller 28F. The measure of the conductivity from the conductivity meter 15F may be used as a measure of the suspended metal content of the fluid in the vessel 22F. The information from the conductivity meter 15F is transmitted to the controller 28F and is used to determine when the fluid has excessive metal content.

It should be appreciated that to minimize the build-up of metal particles in the vessel 22F, a metal separating filter 23F could be used to constantly remove metal particles from the vessel 22F. The meter 15F and the controller 28F can be used to control the operation of the filter 23F.

For the first type of MP-fluid the metal separating filter 23F may be in the form of a magnetic filter to separate the magnetic particles that have not deteriorated from those that have deteriorated and have lost their magnetic properties. The magnetic particles that have not lost their magnetic properties will be recirculated and those that have lost their magnetic properties will be removed. For the second type of MP-fluid the metal separating filter 23F may be replaced with a device to measure the properties of the fluid and when the properties fall below a minimum level the MP-fluid may be drained and replaced.

While the systems 10, 10A, 10B, 10C, 10D, 10E and 10F of FIGS. 1-1F may be satisfactory for polishing a convex surface, it should be appreciated that additional surfaces with varying shapes may well be compatible with the system of the present invention. For example, other orthopaedic implant's articulating surfaces, such as planar surfaces and concave surfaces, may benefit from the polishing by a system of the present invention.

Figure 2:
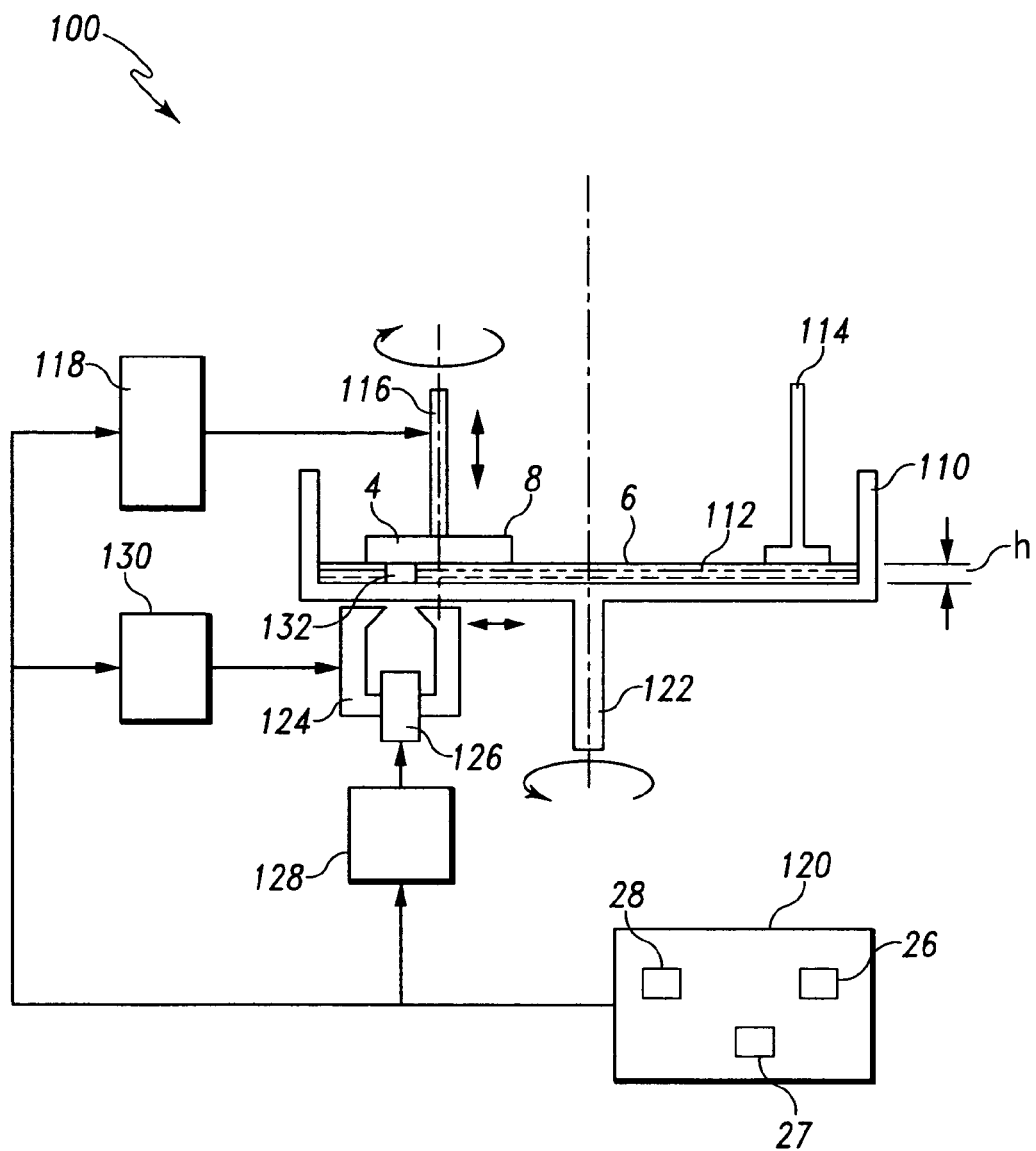
FIG. 2 is a schematic view, partially in cross-section, of another polishing device for use with another embodiment of the present invention for flat work pieces.

For example, and referring now to FIG. 2, a flat or planar articulating surface 6 of an orthopaedic implant 8 may be polished with the use of system 100 of FIG. 2. FIG. 2 is a schematic drawing of the polishing system 100, which may be operated according to the present invention. A cylindrical vessel 110 contains MP-fluid (MP-fluid) 112. In a preferred embodiment, the MP-fluid 112 contains an abrasive. The vessel 110 is preferably constructed of a non-magnetic material, which is inert to the MP-fluid 112.

In FIG. 2, vessel 110 has semi-cylindrically shaped, cross-section, and has a flat bottom. However, the particular shape of the vessel 110 may be modified to suit the work piece to be polished, as we described in greater detail.

An instrument 114, such as a blade, is mounted into vessel 110 to provide continuous stirring of the MP-fluid 112 during polishing. Orthopaedic component, for example tibial tray 8, is connected to a rotatable work piece spindle 116. The work piece spindle 116 is preferably made of a non-magnetic material. The work piece spindle 116 is mounted on a spindle slide 118 and can be moved in a vertical direction. Spindle slide 118 may be driven by a conventional servomotor, which operates according to electrical signals from a programmable control system 120.

The rotation of vessel 110 is controlled by vessel spindle 122, which is preferably positioned in a central location below vessel 110. Vessel spindle 122 can be driven by a conventional motor or by other power source.

An electromagnet 124 is positioned adjacent to vessel 110 so as to be capable of influencing the MP-fluid 112 in a region containing the orthopaedic implant 8. The electromagnet 124 should be capable of inducing a magnetic field sufficient to carry out the polishing operation, and may, for example, include a magnetic field of at least about 100 ka per meter. The electromagnet 124 is activated by winding 126 from a power supply unit 128, which is connected to control system 120. The winding 126 can be any conventional magnetic winding. The electromagnet 124 is set up on an electromagnet slide 130 and can be moved in a horizontal direction, preferably along the radius of vessel 110. It should be appreciated that the strength of magnetic force needed for the particles may be different when utilizing the first type MP-fluid from that used when utilizing the second type MP-fluid.

Electromagnetic slide 130 may be driven by a conventional servomotor, which operates according to electrical signals from the programmable control system 120.

The winding 126 is activated by power supply unit 128 during polishing to induce a magnetic field and influence the MP-fluid 112. Preferably, the MP-fluid 112 is acted on by a non-uniform magnetic field in a region adjacent to the orthopaedic implant 8. In this embodiment, equal intensity lines of the field are normal, or perpendicular, to the gradient of the field. The force of the magnetic field is a gradient directed toward the vessel bottom and normal to the surface of the orthopaedic implant 8. Application of the magnetic field from the electromagnet 124 causes the MP-fluid 112 to change its viscosity and plasticity in a limited polish zone 132 adjacent to the surface being polished. It should be appreciated that the strength of magnetic force needed for the particles may be different when utilizing the first type MP-fluid from that used when utilizing the second type MP-fluid.

The size of the polishing zone 132 is defined by the gap between the pole pieces of the electromagnet 124 and the shape of the tips of the electromagnet 124. Abrasive particles in the MP-fluid are preferably acted upon by the MP-fluid substantially only in the polishing zone 132 and the pressure of the MP-fluid against the surface of the orthopaedic implant 8 is largest in the polishing zone 132.

The composition of the MP-fluid 112 used in the method and devices discussed herein is preferably as described in U.S. Pat. No. 5,449,313. The MP-fluid may include a plurality of magnetic particles, abrasive particles, a stabilizer, and a carrying fluid selected from the group consisting of water and glycerin. The magnetic particles (preferably carbonyl iron particles) are coated with a protective layer of a polymer material, which inhibits their oxidation. The protective layer is preferably resistant to mechanical stress, and as thin as practical. In a preferred embodiment, the coating may be PTFE (Teflon). The particles may be coated by the usual process of micro-capsulization.

The polishing machine, as shown in FIG. 2, can operate as follows. The orthopaedic implant 8 is coupled to workplace spindle 116 in position by spindle slide 118 at a clearance h, with respect to the bottom of the vessel 110 so that, preferably, a portion of the orthopaedic implant 8 to be polished is immersed in the MP-fluid 112. The clearance h may be any suitable clearance that will permit polishing of the work piece. The clearance h will affect the material removal rate for the orthopaedic implant 8. The clearance h will also affect the size of the contact spot at which the polishing zone 132 contacts the orthopaedic implant 8.

The clearance h is preferably chosen so that the surface area of the contact spot is less than ⅓ of the surface area of the orthopaedic implant 8. The clearance h may be changed during the polishing process.

The orthopaedic implant 8 and the vessel 110 may both be rotated. For example, the orthopaedic implant 8 and the vessel 110 may be rotated opposite to each other. The vessel spindle 122 is put into rotating motion, thereby rotating the vessel 110. The vessel spindle 122 rotates about a central axis and preferably rotates vessel 110 at a speed sufficient to affect polishing, but insufficient to generate a centrifugal force sufficient to substantially spin or spray the MP-fluid 112 out of the vessel 110.

The vessel 110 may be rotated at a constant velocity. The motion of the vessel 110 provides continuous delivery of a fresh portion of the MP-fluid 112 to the region where the orthopaedic implant 8 is located and provides continuous motion of the MP-fluid 112 in contact with the surface of the orthopaedic implant being polished in the polishing zone 132. It should be appreciated that additional carrying fluid, preferably water or glycerin, is added during the polishing to replenish carrying fluid that has vaporized, thus maintaining the properties of the fluid.

The work piece spindle 116 may also be rotated about a central axis to provide rotating movement to the orthopaedic implant 8. The work piece spindle 116 operates in speeds, for example up to 2,000 RPM, with about 500 RPM being typical. The motion of the work piece spindle 116 continuously brings a fresh part of the surface of the orthopaedic implant 8 into contact with the polishing zone 132, so that material removal along the circumference of the surface being polished will be substantially uniform.

As abrasive particles in the MP-fluid 112 contact the surface 6 of the orthopaedic implant 8, a re-shaped area having the width of the polishing zone is gradually polished on the surface 6 of the orthopaedic implant 8. Polishing is accomplished in one or more cycles, with an incremental amount of material removed from the orthopaedic implant in each cycle. The polishing zone moves through the ring-shaped area once during each cycle as the orthopaedic implant is rotated. Polishing of the whole surface of the orthopaedic implant 8 is achieved by radial displacement of the electromagnet 124 using the electromagnet slide 130, which causes the polishing zone 132 to move relative to the work piece surface.

Figure 3:
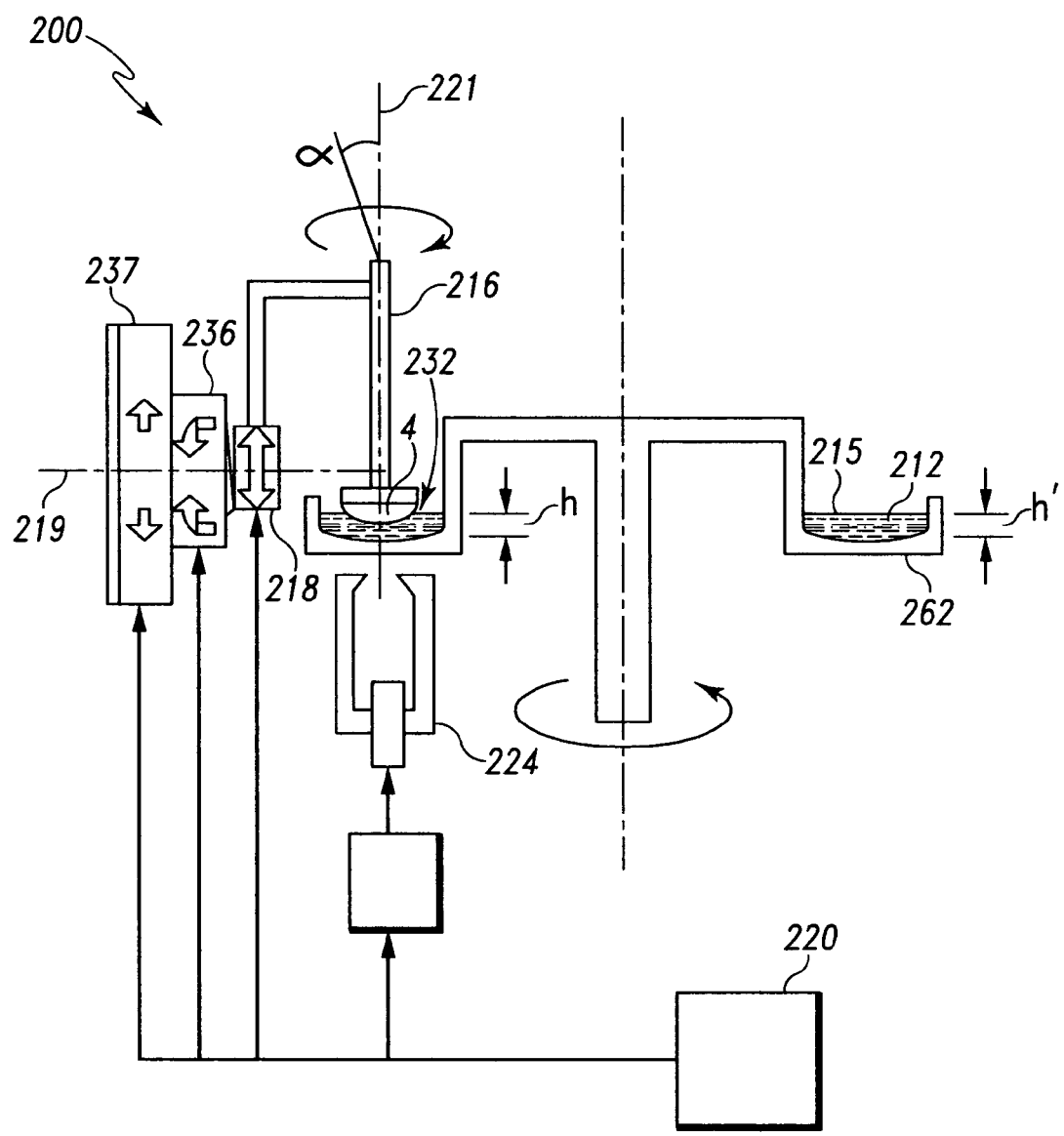
FIG. 3 is a schematic view, partially in cross-section, of another polishing device for use with another embodiment of the present invention for use with convex work pieces.

Referring now to FIG. 3, yet another embodiment of the present invention is shown as system 200. System 200 is similar to the system 100 of FIG. 2, except that the system 200 is adapted for highly efficient polishing of convex work pieces. For example, and as shown in FIG. 3, the system 200 is adapted for use with, for example, work piece 4 in the form of an orthopaedic hip head. As shown in FIG. 3, the system 200 includes a vessel 262, which is in the form of a circular cup. The radius of curvature of the internal wall adjacent to polishing zone 232 is larger than the largest radius of curvature of the orthopaedic component 4.

During polishing, it is desirable to minimize the movement of MP-fluid 212 relative to the vessel 262. To minimize the movement or slippage of the MP-fluid 212, the internal wall of the vessel 262 may be covered with a layer of a nap of porous material 215 to provide reliable mechanical adhesion between MP-fluid 212 and the wall of the vessel 262. Work piece spindle 216 is connected with spindle slide 218, which is connected to rotatable table 236. The rotatable table 236 is connected to a table slide 237.

Spindle slide 218, rotatable table 236, and table slide 237 may be driven by conventional servomotors, which operate according to electrical signals from programmable control system 220. Rotatable table 236 permits work piece spindle 216 to be continuously rotated about its horizontal axis 219, or permits its positioning at an angle $\alpha$ with the initial vertical axis 221 of spindle 216. The horizontal axis 219 preferably is located at the center of curvature f the polished surface at the initial vertical position of the work piece spindle 216.

Spindle slide 218 permits vertical displacement h' of the center of the polished surface curvature relative to axis 219. Table slide 237 moves the rotatable table 236 with spindle slide 218 and work piece spindle 216 to obtain and maintain the desired clearance h between the polished surface of the work piece or orthopaedic implant 4 and the bottom of the vessel 262.

An electromagnet 224 may be stationary and positioned below the vessel 262 such that its magnetic gap is symmetric about the work piece spindle axis 221 when this axis is perpendicular to the plane of the polishing zone 232. It should be appreciated that the strength of magnetic force needed for the particles may be different when utilizing the first type MP-fluid from that used when utilizing the second type MP-fluid.

Figure 4:
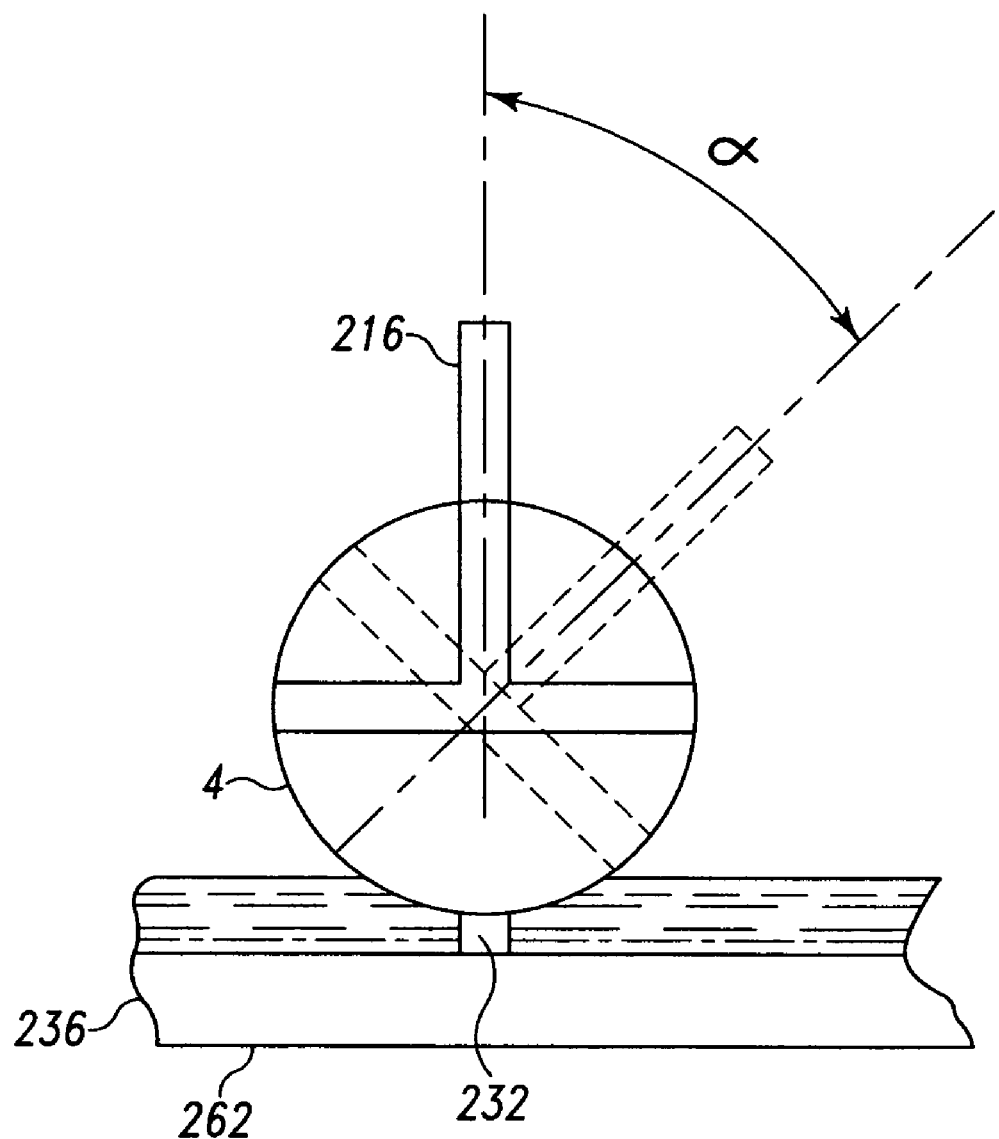
FIG. 4 is an enlarged view of a portion of the apparatus of FIG. 3.

The polishing machine for the system 200 as shown in FIG. 4 operates as follows. To polish the orthopaedic implant 4, work piece spindle 216 with attached orthopaedic implant 4 is positioned so that the center of the radius of curvature of the orthopaedic implant 4 is brought into coincidence with the pivotal point or rotation of axis 219 of the rotatable table 236. The removal rate for the orthopaedic implant to be polished is then determined experimentally using a test work piece similar to the orthopaedic implant to be polished. Polishing of the orthopaedic implant 4 may then be conducted automatically by moving its surface relative to the polishing zone 232 using rotatable table 236 (see FIG. 3) which rocks work piece spindle 216 and changes the angle $\alpha$ according to calculated regimes of treatment.

Figure 5:
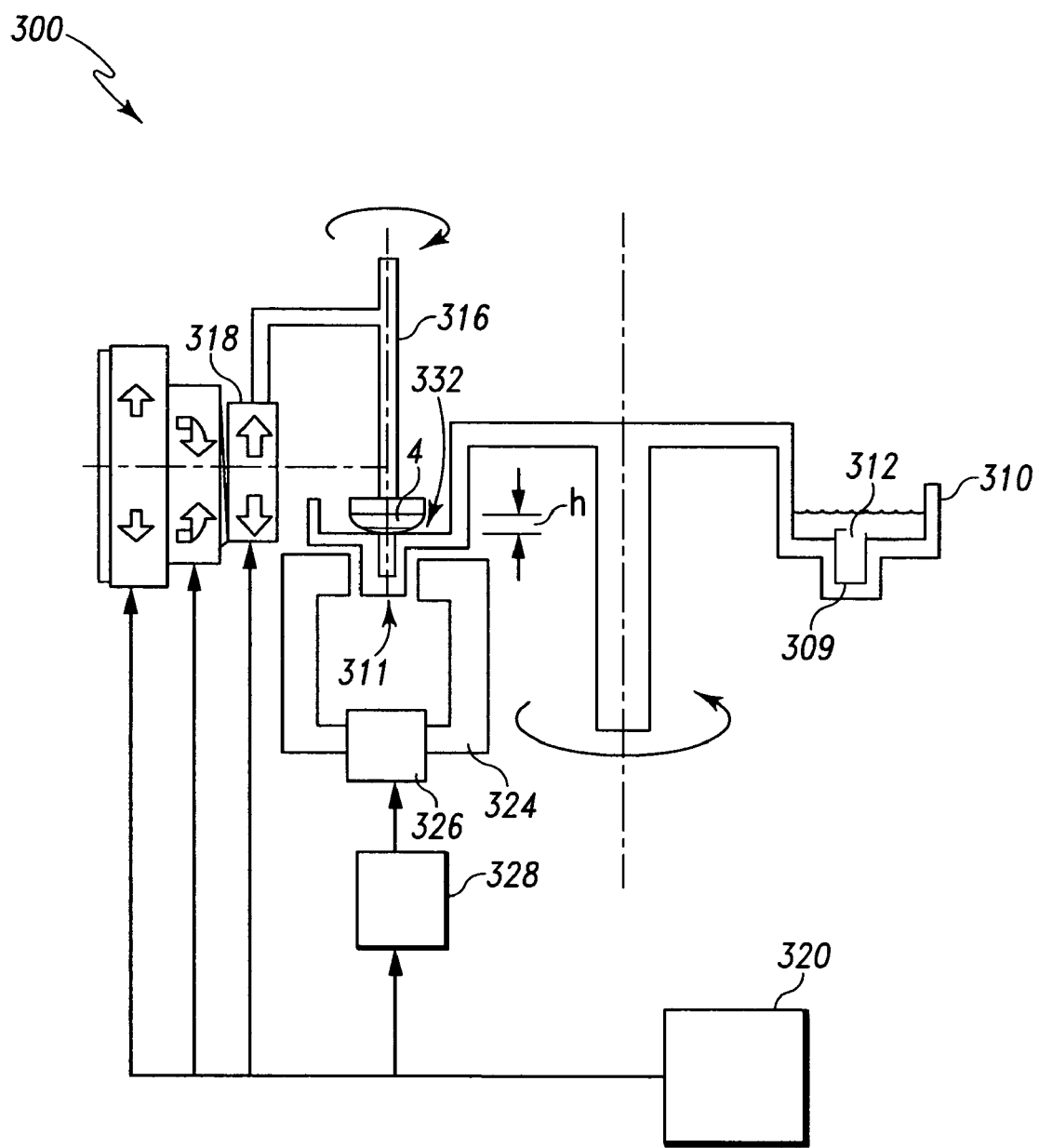
FIG. 5 is a cross-sectional side view of a polishing device for use with an embodiment of the present invention.

Referring now to FIG. 5, yet another embodiment of the present invention is shown as system 300. System 300 is similar to system 200 of FIG. 3, except that system 300 includes a vessel 310 that has an additional ring-shaped trough 309, which passes through gap 311 of electromagnet 324. It should be appreciated that the strength of magnetic force needed for the particles may be different when utilizing the first type MP-fluid from that used when utilizing the second type MP-fluid. This configuration of the internal wall of the vessel 310 results in a smaller, more focused, polishing zone 332. The configuration also results in an increase in adhesion between the MP-fluid 312 and the vessel 310. The smaller, more focused, polished zone results in a smaller contact spot. In all other respects, the embodiment depicted in FIG. 5 is the same as that depicted in FIG. 3.

Figure 6:
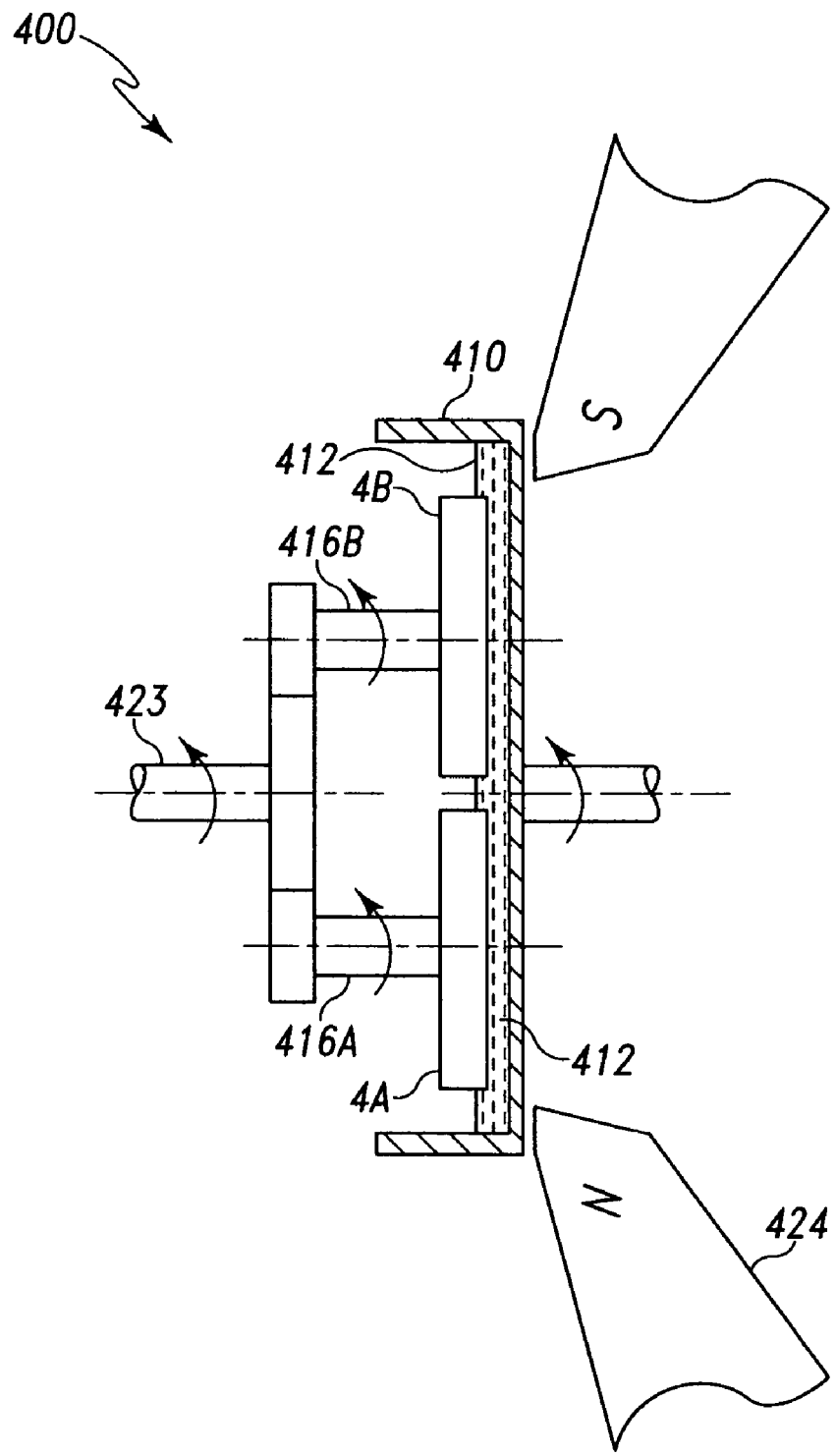
FIG. 6 is a cross-sectional side view of a polishing device for use with another embodiment of the invention.

Referring now to FIG. 6, yet another embodiment of the present invention is shown as system 400. System 400 is similar to system 100 of FIG. 2, except that the system 400 allows for multiple objects to be polished simultaneously, thereby increasing the productive capacity of the system. For the system 400, as shown in FIG. 6, an MP-fluid 412 is placed into a cylindrical vessel 410. Orthopaedic implants to be polished in the form of, for example tibial trays 4A and 4B or other orthopaedic implants with a planar surface to polish, are fixed on spindles, for example as shown, a first orthopaedic implant 4A is placed on first spindle 416A and similarly a second orthopaedic implant 4B is placed on second spindle 416B. The spindles 416A and 416B are mounted on a disc 423 capable of rotating in the horizontal plane. An electromagnet 424 is installed under the vessel 410 such that it creates a magnetic field along the entire surface of the vessel 410. It should be appreciated that the strength of magnetic force needed for the particles may be different when utilizing the first type MP-fluid from that used when utilizing the second type MP-fluid.

Disc 423, vessel 410 and the orthopaedic implants to be polished 4A and 4B are put into rotation in the same or opposite directions with equal or different speeds. By regulating the magnetic field intensity and the rotation of the disc, the vessel and the objects, the rate of removal of material from the surface of the object to be polished is controlled.

Figure 7:
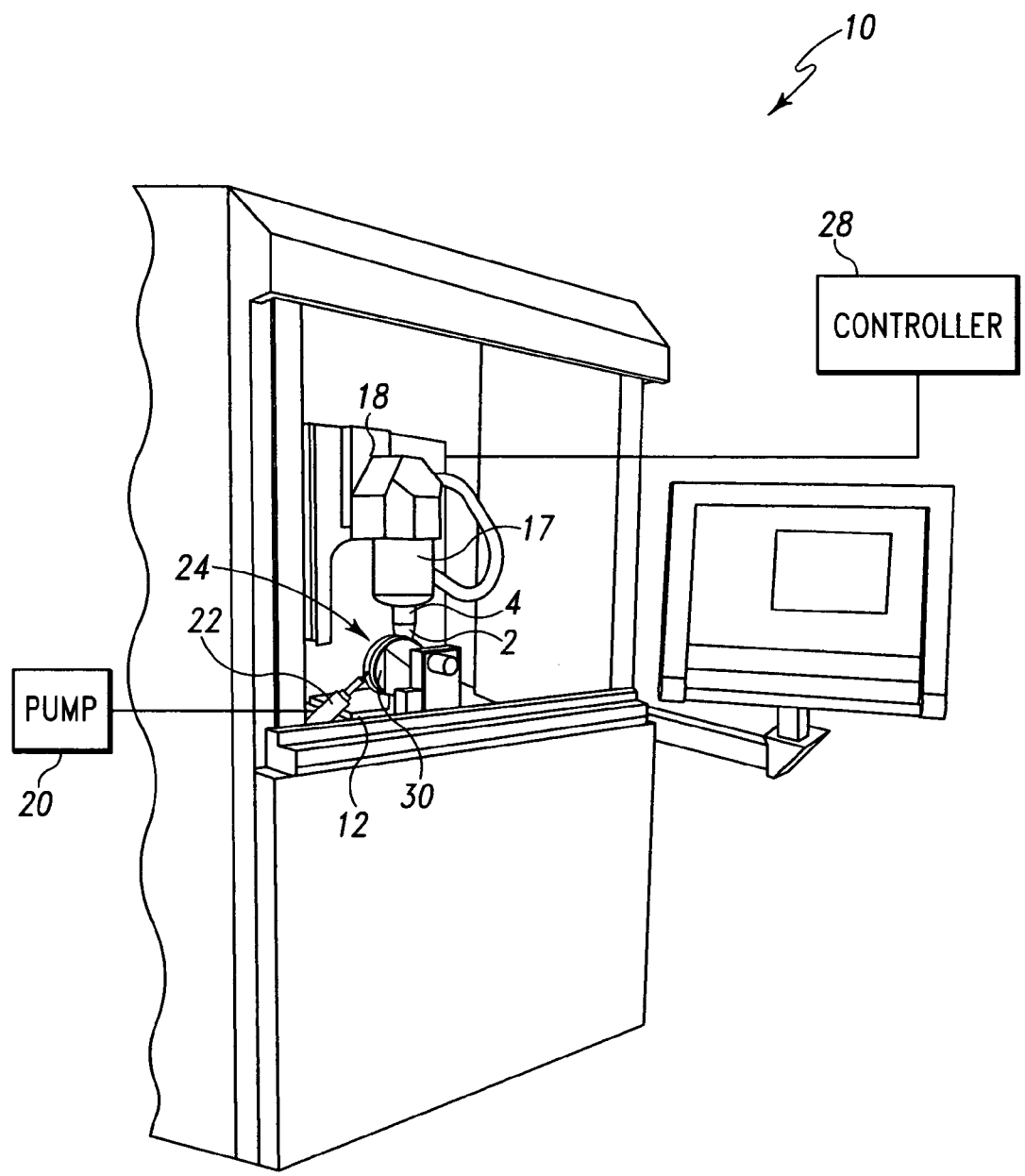
FIG. 7 is a perspective view of a polishing machining that may be utilized in performing the present invention.
Figure 8:
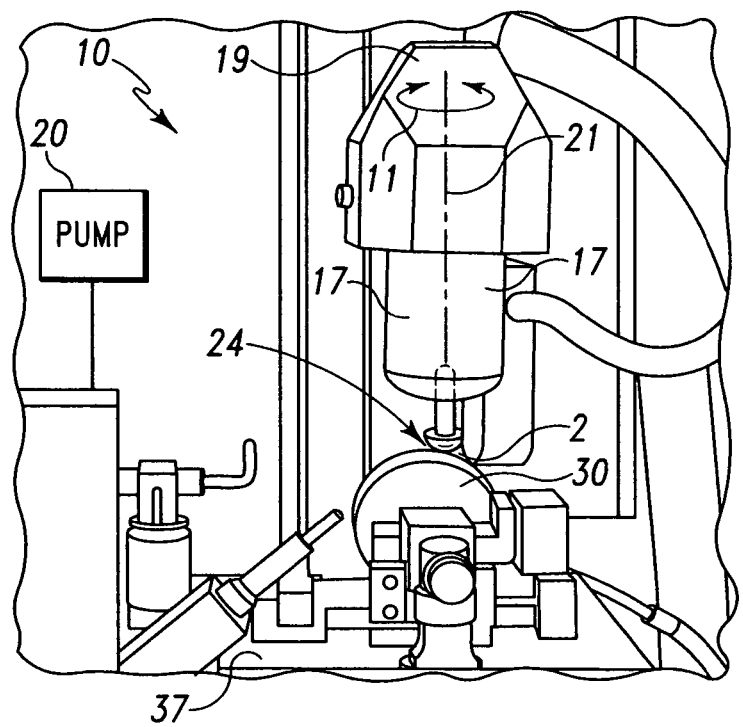
FIG. 8 is a partial perspective view of the polishing machining of FIG. 7.
Figure 9:
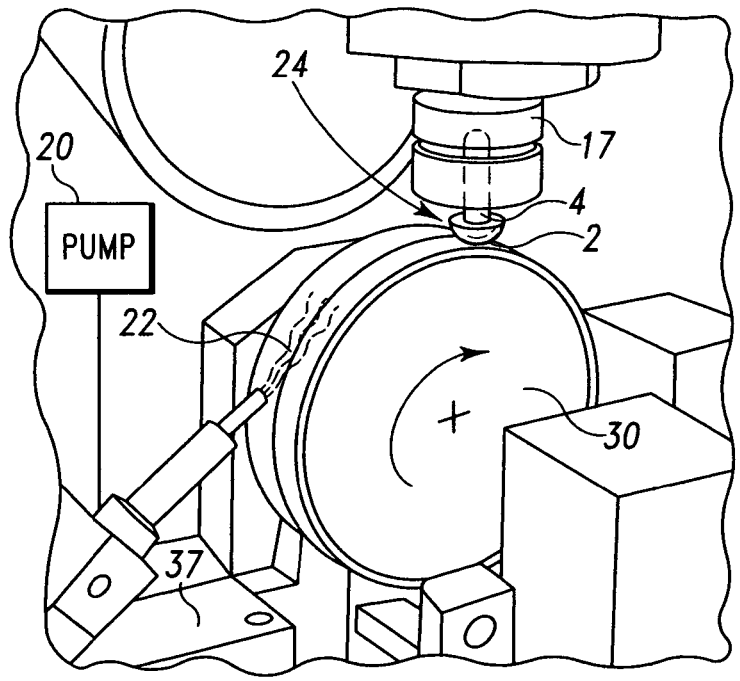
FIG. 9 is an enlarged partial perspective view of the polishing machining of FIG. 7.

Referring now to FIGS. 7, 8 and 9, the system 10 is shown in the form of a polishing machine adapted for polishing convex articulating surfaces of orthopaedic implants. The polishing machine 10, as shown in FIG. 7, includes a work piece spindle 17 for securing the orthopaedic implant component 4. The polishing machine 10 further includes a spherical wheel 30 to which the fluid path 22 is directed. Fluid from fluid conditioner 12 is pumped by pump 20 along fluid path 22 to polishing zone 24 adjacent the articulating surface 2 of the orthopaedic implant 4. A spindle slide 18 advances the orthopaedic implant 4 into contact with the polishing zone 24 to commence the polishing of the articulating surface 2 of the orthopaedic implant 4.

Referring now to FIGS. 8 and 9, the polishing zone 24 is shown in greater detail. The fluid path 22 extends from the pump 20 to the polishing zone 24. The polishing zone 24 is adjacent the articulating surface 2 of the orthopaedic implant 4. A work piece spindle 17 is used, as shown in FIGS. 8 and 9, to rotate the orthopaedic implant 4 about vertical axis 21. It should be appreciated that the vertical axis 21 may be changed to accommodate the external convex periphery of the articulating surface 2 of the orthopaedic implant 4. The work piece spindle 17, as shown in FIG. 8, may rotate in the direction of arrows 11 about centerline 21 to obtain a different angle(s) θ of the orientation of the work piece spindle 17 with respect to the vertical axis.

Referring now to FIG. 10, the orthopaedic implant in the form of orthopaedic component 4 is shown in greater detail. The orthopaedic component 4 is in the form of a convex orthopaedic implant in the form of a head 6. The head 6 has a generally spherical articulating surface 5. The prosthetic component, as shown in FIG. 10, is in the form of hip stem 9. The hip stem 9 includes a stem portion 7 to which head 6 may be removably attached.

Figure 11:
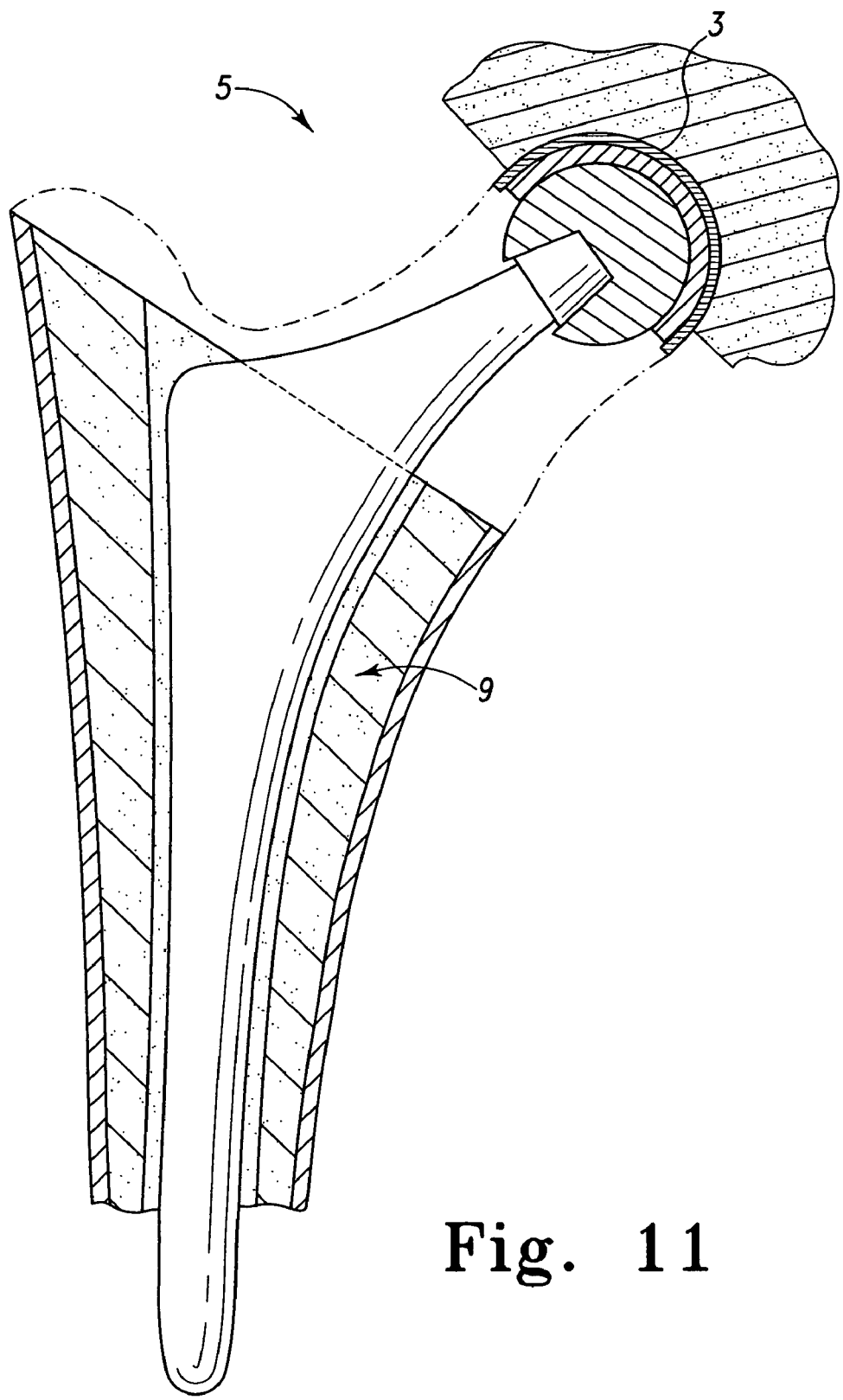
FIG. 11 is a plan view of the hip stem of FIG. 10 implanted in a femur.

Referring now to FIG. 11, the hip stem 9 is shown in connection with a cup 3 to form a hip prosthesis 5. The hip prosthesis 5 includes the hip stem 9 as well as cup 3.

Figure 12:
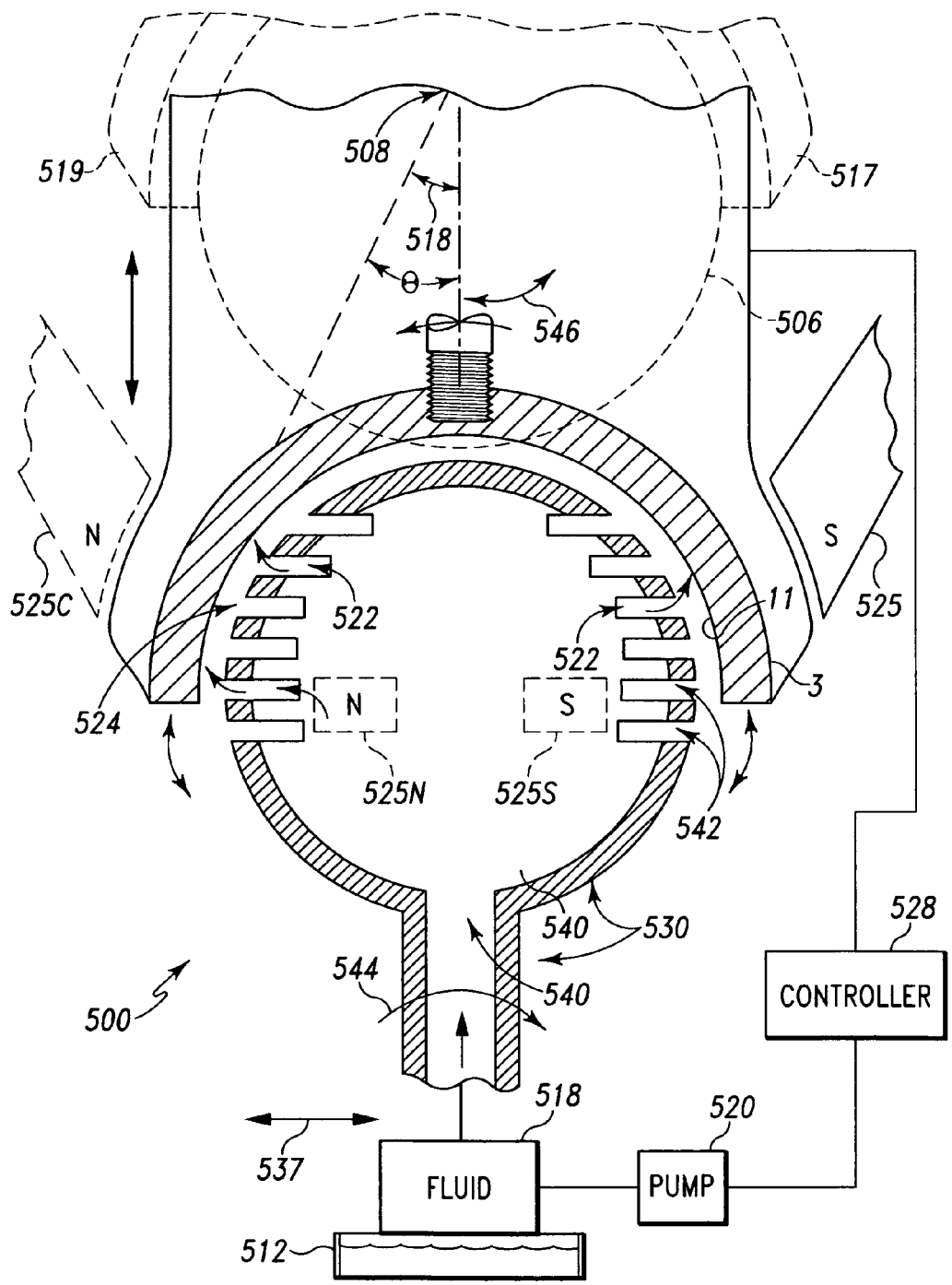
FIG. 12 is a partial plan view partially in cross-section of a polishing device for cooperation with an internal periphery of a hip cup in accordance with an embodiment of the present invention.

Referring now to FIG. 12, yet another embodiment of the present invention is shown as system 500. System 500 is adapted for use in polishing concave surfaces. For example, the system 500 is suitable for polishing the articulating surface 11 of cup 3 of a hip cup prosthesis. It should be appreciated that the system 500 may also be used to polish concave surfaces of vertebral implants such as those of FIGS. 18 and 18A or glenoid components. The system 500 is somewhat similar to the system 100 of FIGS. 1, 7, 8, and 9, except that the system 500 utilizes a ball 530 to replace the spherical drum wheel 30 of the system 10.

The system 500 includes a fluid conditioner 512 for receiving MP-fluid 518. The fluid 518 is caused to flow by pump 520 along fluid path 522 to polishing zone 524 adjacent the articulating surface 11 of the cup 3. The fluid path 522 includes a path through internal cavities 540 of the ball 530. The ball 530, as shown in FIG. 12, includes a plurality of openings or slits 542, which permit the MP-fluid 518 to pass from the internal cavities 540 of the ball 530 to the polishing zone 524.

Preferably, as shown in FIG. 12, the ball 530 rotates in the direction of arrow 544 while the cup 3 is located and mounted on spindle 517, which rotates in the direction of arrow 546. The spindle 517 preferably rotates opposed to the direction of rotation 544 of the ball 530. The spindle 517, as shown in FIG. 12, may be permitted to translate vertically by means of spindle slide 519. While the ball 530 may successfully polish the cup 3 without any angular motion between the cup 3 and the ball 530, preferably and as shown in FIG. 12, the spindle 517 is able to rotate in the direction of arrow 518 about origin 508 to form angle θ such that an additional portion of the ball 530 may be positioned within the inner-concave periphery of the cup 3. The rotation of the spindle 517 about origin 508 is accomplished by mounting the spindle 517 to a rotating head 506 that in turn is mounted on spindle slide 519. Thus, the cup 3 can be exposed to more surfaces for polishing.

The angular rotation of the cup 3 relative to the ball 530 may be accomplished by a combination of vertical movements of the spindle slide 519 and horizontal motions of table slide 537 as well as by rotation of the rotating head 506. The ball 530 moving horizontally with the table slide 537 in the spindle and the cup 3 moving vertically with the spindle slide 519 and rotating with the rotating head 506. The relative motions of the spindle slide 519 and table slide 537 may for example, be controlled by controller 528. Similarly, the pump 520 as well as the rotation of the ball 530 and the spindle 517, may be controlled by controller 528.

The system 500 of FIG. 12 preferably includes a magnetic field for permitting the MP-fluid 518 to act as described in the present invention. For example, and as shown in FIG. 12, the ball 530 may act as, for example, a north pole and south pole 525 may be utilized in a spaced apart relationship from the ball 530. Alternatively, the magnetic poles may be spaced from the ball 530. For example, a first external pole working as a north pole may be in the form of pole 525C as shown in phantom. The second or south magnetic pole 525 may be positioned in a spaced apart relationship from the first magnetic pole 525C. Alternatively, a pair of magnetic poles, such as south magnetic pole 525S and north magnetic pole 525N may, as show in phantom, be located with the ball 530. It should be appreciated that the strength of magnetic force needed for the particles may be different when utilizing the first type MP-fluid from that used when utilizing the second type MP-fluid.

Figure 12A:
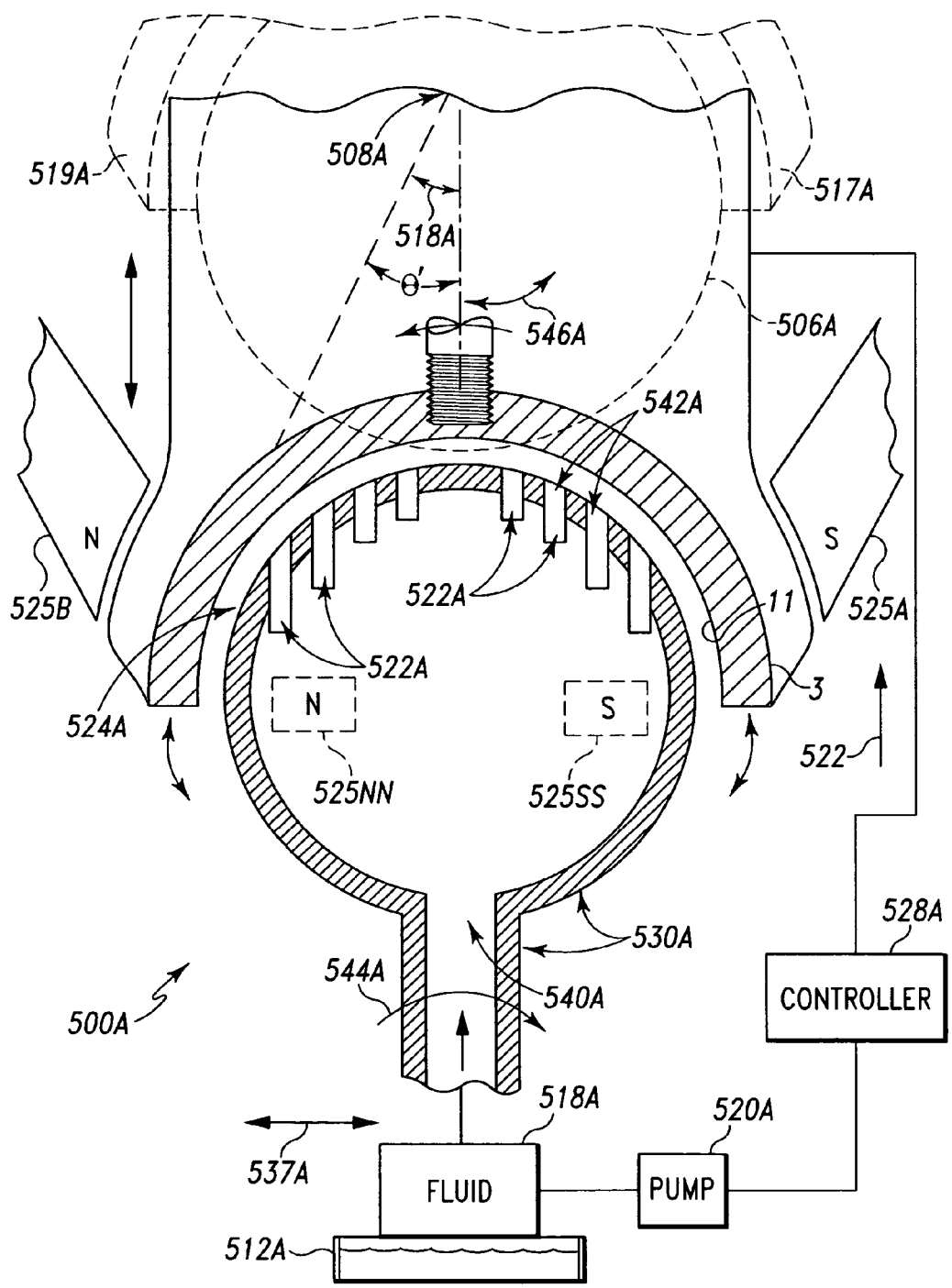
FIG. 12A is a partial plan view partially in cross-section of a polishing device for cooperation with an internal periphery of a hip cup similar to that of FIG. 12 except that the slits are vertical rather than horizontal in accordance to another embodiment of the present invention.

Referring now to FIG. 12A, yet another embodiment of the present invention is shown as system 500A. The system 500A is adapted for use in polishing concave surfaces and it similar to the system 500 of FIG. 12. The system 500A is suitable for polishing the articulating surfaces of concave surfaces, for example, the articulating surface 11 of cup 3 of a hip cup prosthesis. The system 500A is somewhat similar to the system 500 of FIGS. 1, 7, 8, and 9, except that the system 500A utilizes a ball 530A to replace the spherical drum wheel 30 of the system 10. The system 500A uses a fluid conditioner 512A for receiving MP-fluid 518A.

For the first type of MP-fluid the conditioner 512A may be in the form of a magnetic filter to separate the magnetic particles that have not deteriorated from those that have deteriorated and have lost their magnetic properties. The magnetic particles that have not lost their magnetic properties will be recirculated and those that have lost their magnetic properties will be removed. For the second type of MP-fluid the conditioner may merely measure the properties of the fluid and when the properties fall below a minimum level the MP-fluid may be drained and replaced.

The fluid 518A is caused to flow by pump 520A along fluid path 522A to polishing zone 524A adjacent the articulating surface 11 of the cup 3. The fluid path 522A includes a path through internal cavities 540A of the ball 530A. The ball 530A, as shown in FIG. 12A, includes a plurality of openings or slits 542A that, as shown in FIG. 12A, are generally horizontal. The slits 542A permit the MP-fluid 518A to pass from the internal cavities 540A of the ball 530A to the polishing zone 524A.

Preferably, and as shown in FIG. 12A, the ball 530A rotates in the direction of arrow 544A, while the cup 3 is located and mounted on spindle 517A. The spindle 517A rotates in the direction of arrow 546A. The spindle 517A preferably rotates opposed to the direction of rotation 544A of the ball 530A. The spindle 517A, as shown in FIG. 12A, may be permitted to translate vertically by means of spindle slide 519A.

While the ball 530A may successfully polish the cup 3 without any angular motion between the cup 3 and the ball 530A, preferably and as shown in FIG. 12A, the spindle 517A is able to rotate in the direction of arrow 518A about origin 508A to form angle θ' such that an additional portion of the ball 530A may be positioned within the inner-concave periphery of the cup 3. The rotation of spindle 517A about origin 508A is accomplished by mounting the spindle 517A to rotating head 506A that in turn is mounted on spindle slide 519A. Thus, the cup 3 can be exposed to more surfaces for polishing.

The angular rotation of the cup 3 relative to the ball 530A may be accomplished by a combination of vertical movements of the spindle slide 519A and the horizontal motions of table slide 537A, as well as by rotation of the rotating head 506A. The ball 530A moving horizontally with the table slide 537A and the spindle 517A, and the cup 3 moving vertically with the spindle slide 519A and rotating with the rotating head 506A. The relative motion of the spindle slide 519A and the table slide 537A may, for example, be controlled by controller 528A. Similarly, the pump 520A, as well as the rotation of the ball 530A and the spindle 517A, may be controlled by controller 528A.

To properly excite the MP-fluid, the MP-fluid 518A is affected by a magnetic field. Such magnetic field may be accomplished in any suitable manner. For example, and as shown in FIG. 12A, the ball 530A may form as a magnet, for example, a north pole. The system 500A may further include a south or second magnetic pole 525A positioned spaced from the ball 530A to provide a magnetic field between the north and south poles 530A and 525A respectively. It should be appreciated that the strength of magnetic force needed for the particles may be different when utilizing the first type MP-fluid from that used when utilizing the second type MP-fluid.

Alternatively, the MP-fluid 518A may be exposed to a magnetic field by a pair of north and south magnetic fields external to the ball 530A. For example, as shown in FIG. 12A, a second north magnetic pole 525B and the south pole 525A may be used. Alternatively, a pair of magnetic poles such as south magnetic pole 525SS and north magnetic pole 525NN may, as shown in phantom, be located within the ball 530A.

Figure 13:
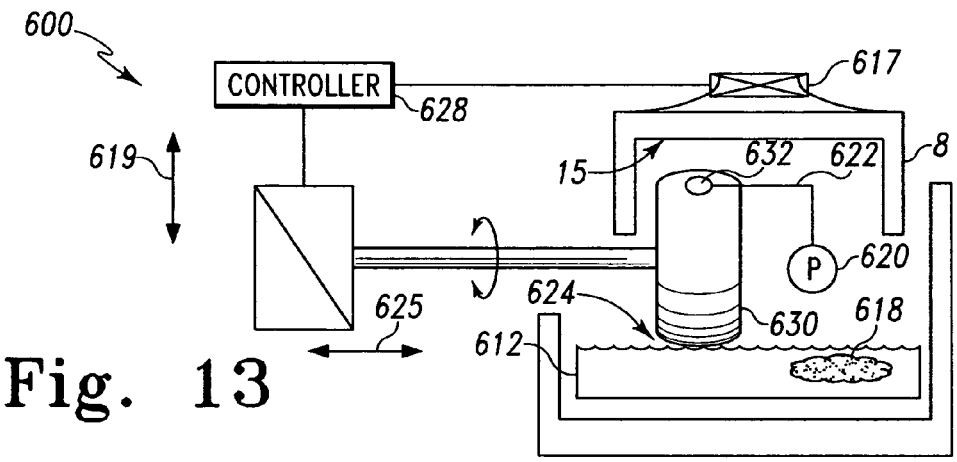
FIG. 13 is a partial plan view partially in cross-section of lapping wheel for cooperation with a recessed face of a knee tibial tray in accordance with another embodiment of the present invention.

Referring now to FIG. 13, yet another embodiment of the present invention is shown as system 600. The system 600 is similar to the system 100 of FIG. 1, except that the spherical drum 30 of the system 100 is replaced with a generally cylindrical lapping wheel 630. The lapping wheel 630 is rotated by a spindle (not shown) and used to provide a lapping surface with recessed surface 15 of tibial tray 8. Tibial tray 8 includes recessed surface 15, which must be polished. A polishing of the recessed surface 15 is quite troublesome in that tools are not generally available to polish the surface 15. The lapping wheel 630 is caused to translate vertically by vertical slide 619 as well as horizontally by horizontal slide 625. MP-fluid 618 conditioned by fluid conditioner 612 is pumped by pump 620 through conduit 622 to polishing zone 632.

For the first type of MP-fluid the conditioner 612 may be in the form of a magnetic filter to separate the magnetic particles that have not deteriorated from those that have deteriorated and have lost their magnetic properties. The magnetic particles that have not lost their magnetic properties will be recirculated and those that have lost their magnetic properties will be removed. For the second type of MP-fluid the conditioner may merely measure the properties of the fluid and when the properties fall below a minimum level the MP-fluid may be drained and replaced.

Figure 13A:
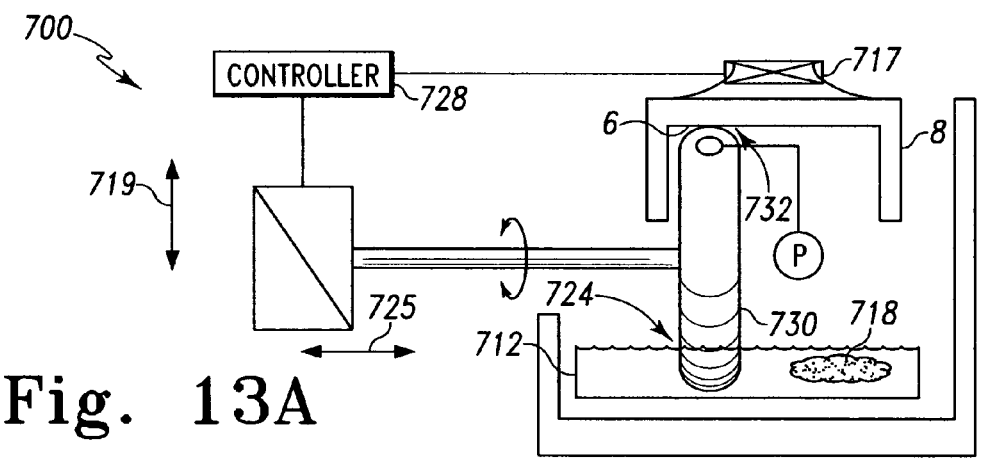
FIG. 13A is a partial plan view partially in cross-section of another lapping wheel for cooperation with a recessed face of a knee tibial tray in accordance with yet another embodiment of the present invention.

Referring now to FIG. 13A, yet another embodiment of the present invention is shown as system 700. System 700 is similar to system 100 of FIG. 2, except that a lapping wheel 730 is positioned between vessel 712 and work piece in the form of tibial tray 8. The lapping wheel 730 draws MP-fluid 718 from the vessel 712 and applies the fluid 718 to polishing zone 732 between the articulating surface 6 of the tibial tray 8 and wheel 730.

A spindle 717 rotates the tibial tray 8 while a horizontal slide 725 advances the lapping wheel 730 horizontally and a vertical slide 719 permits the movement of the slide vertically. A controller 728 controls the motion of the horizontal slide 725, the vertical slide 719, the spindle 717 as well as the lapping wheel 730 to properly lap the articulating surface 6 of the tibial tray 8.

Figure 13B:
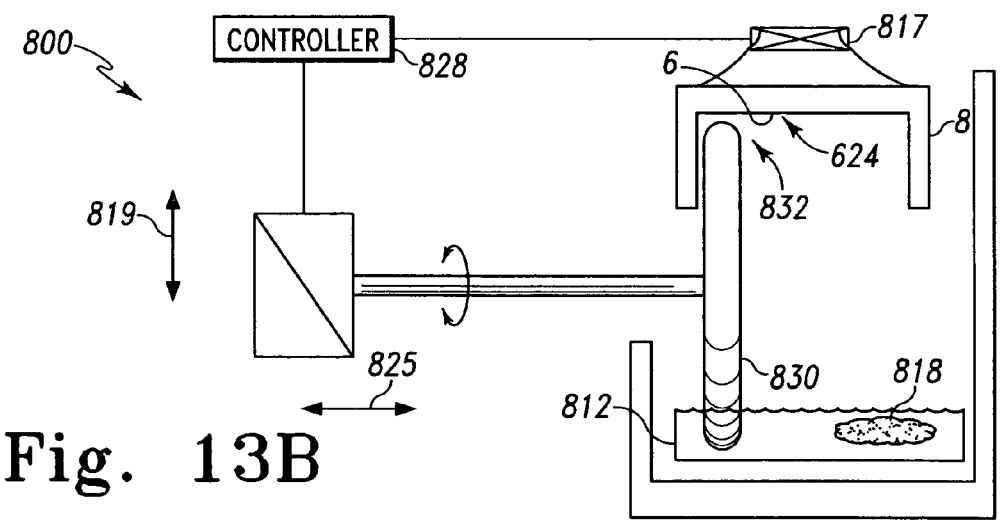
FIG. 13B is a partial plan view partially in cross-section of yet another lapping wheel for cooperation with a recessed face of a knee tibial tray in accordance with a further embodiment of the present invention.

Referring now to FIG. 13B, yet another embodiment of the present invention is shown as system 800. The system 800 is similar to the system 700 of FIG. 13A, but includes lapping wheel 830 that is larger and diameter and narrower than the lapping wheel 730 of the system 700. Again, a tibial tray 8 has its articulating surface 6 polished by the lapping wheel 830. MP-fluid 818 from the vessel 812 is advanced by the lapping wheel 830 to the polishing zone 832 where the MP-fluid 818 is utilized to lap the articulating surface 6. A horizontal slide 825 and a vertical slide 819 are utilized to position the lapping wheel 830 about the articulating surface 6. A controller 828 is used to control the positioning of the vertical slide 819, the horizontal slide 825, the spindle 817, and the lapping wheel 830.

Figure 14:
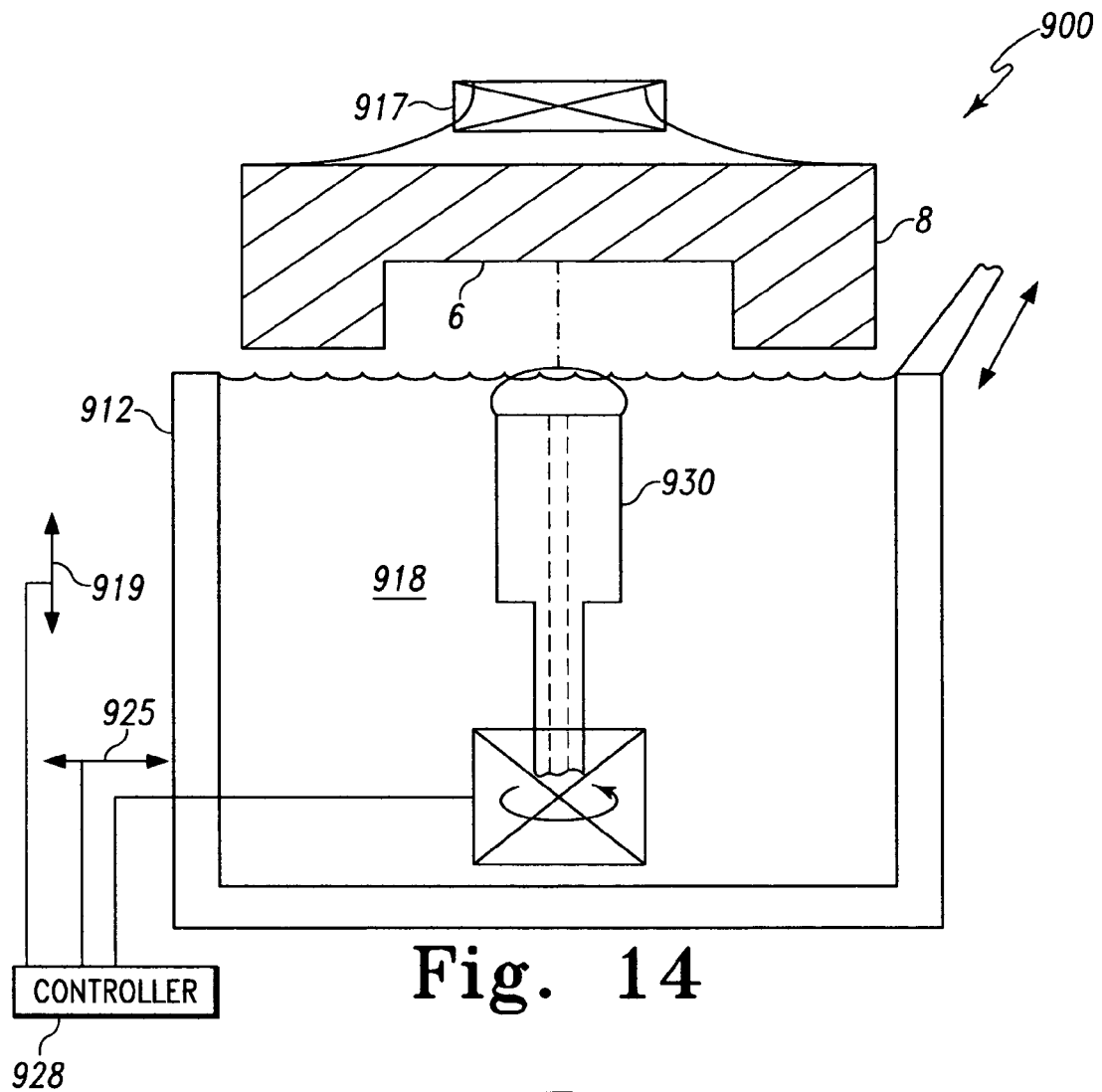
FIG. 14 is a partial plan view partially in cross-section of lapping tool for cooperation with a recessed face of a knee tibial tray in accordance with another embodiment of the present invention.

According to the present invention, and referring now to FIG. 14, yet another embodiment of the present invention is shown as system 900. The system 900 is similar to the system 800 of FIG. 13B, except that lapping wheel 930 is mounted vertically and that the lapping wheel 930 is small in diameter. The system 900 provides for lapping at the end of the lapping wheel 930. The lapping wheel 930 is positioned in vessel 912, which is filled with MP-fluid 918. Horizontal slide 925 and vertical slide 919 are controlled by controller 928, which also controls the rotation of the lapping wheel 930 and the work piece spindle 917.

Figure 15:
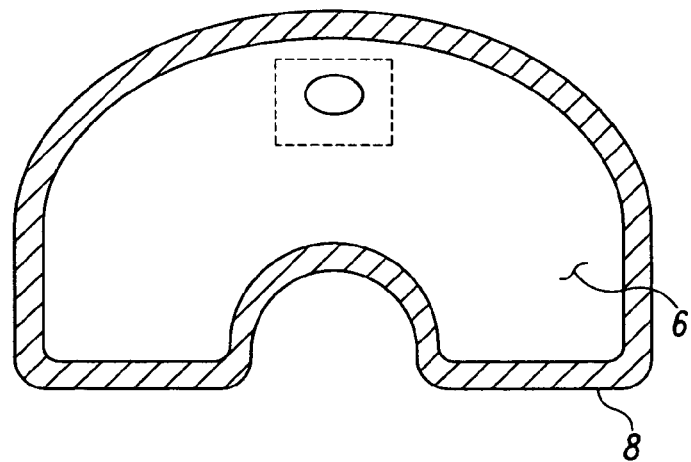
FIG. 15 is a top view of a knee tibial tray for use in performing orthopaedic surgery that may be machined in accordance with yet another embodiment of the present invention.

Referring now to FIG. 15, tibial tray 8 is shown in greater detail. The tibial tray 8 includes the recessed surface 6, which is polishable by the polishing system of the present invention.

Figure 16:
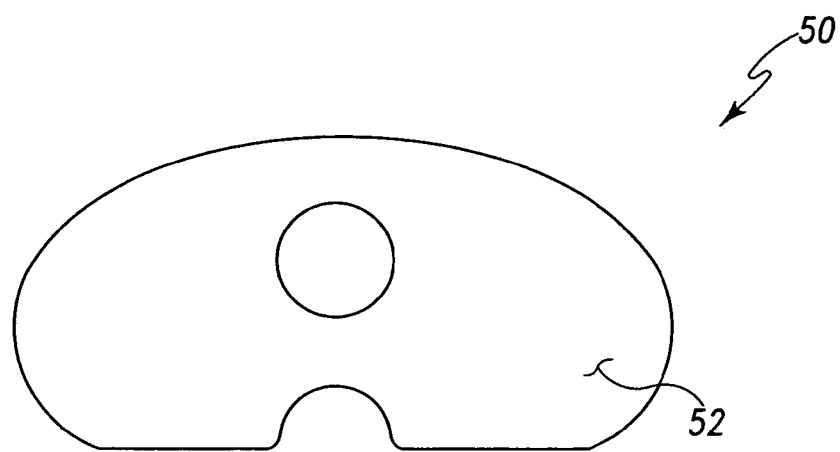
FIG. 16 is a top view of another knee tibial tray for use in performing orthopaedic surgery that may be machined in accordance with yet another embodiment of the present invention.
Figure 17:
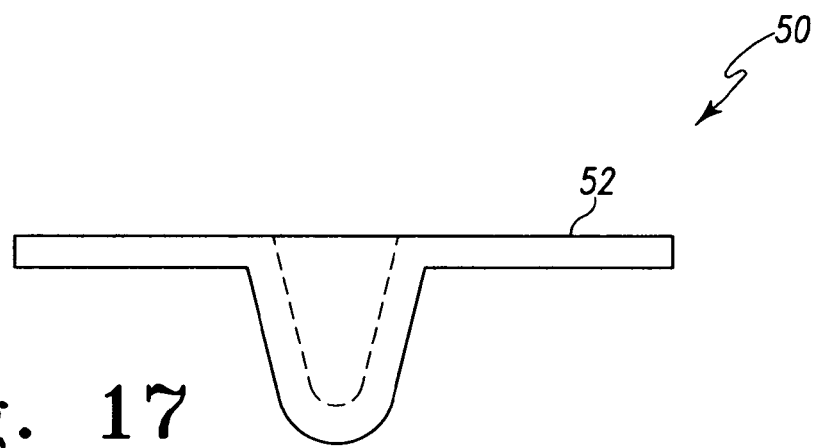
FIG. 17 is a plan view of the knee tibial tray of FIG. 16.

Referring now to FIGS. 16 and 17, yet another prosthetic component to be polished by the system of the present invention is shown as tibial tray 50. The tibial tray 50 includes an articulating surface 52. The surface 52, as shown in FIGS. 16 and 17, is planar. Therefore, the system, such as system 100 of FIG. 2, is suitable for polishing the articulating surface of the tibial tray 50 of FIGS. 16 and 17.

Figure 17A:
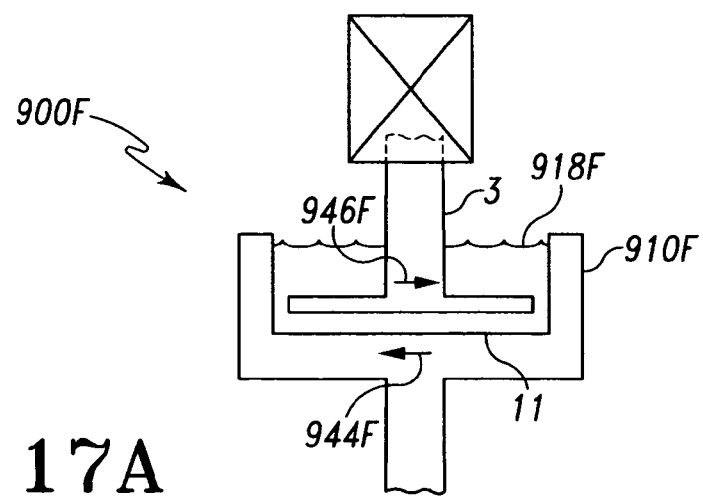
FIG. 17A is a schematic drawing of a polishing device for cooperation with the bearing surface of the knee tibial tray of FIG. 17.

Referring now to FIG. 17A, yet another embodiment of the present invention is shown as system 900F. The system 900F is adapted for use in polishing planar surfaces, for example, knee tibial surfaces. The system 900F is somewhat similar to the system 100 of FIG. 2. The system 900F includes a vessel 910F for storing the MP-fluid 918F. The bearing surface of the knee tibial component 3 is immersed in the MP-fluid 918F in the vessel 910F.

Preferably, and as shown in FIG. 17A, the knee tibial component 3 rotates in the direction of arrow 946F. The vessel 910F rotates in the direction of arrow 944F. The knee tibial component 3 preferably rotates in a direction opposed to the direction of rotation 944F of the vessel 910F.

System 900F of FIG. 17A further includes components capable of providing a magnetic field for the MP-fluid 918F. For example, the system 900F may include magnets such as those of FIG. 18C, the magnets may, for example, be electromagnetic magnets. It should be appreciated that the strength of magnetic force needed for the particles may be different when utilizing the first type MP-fluid from that used when utilizing the second type MP-fluid.

Figure 18:
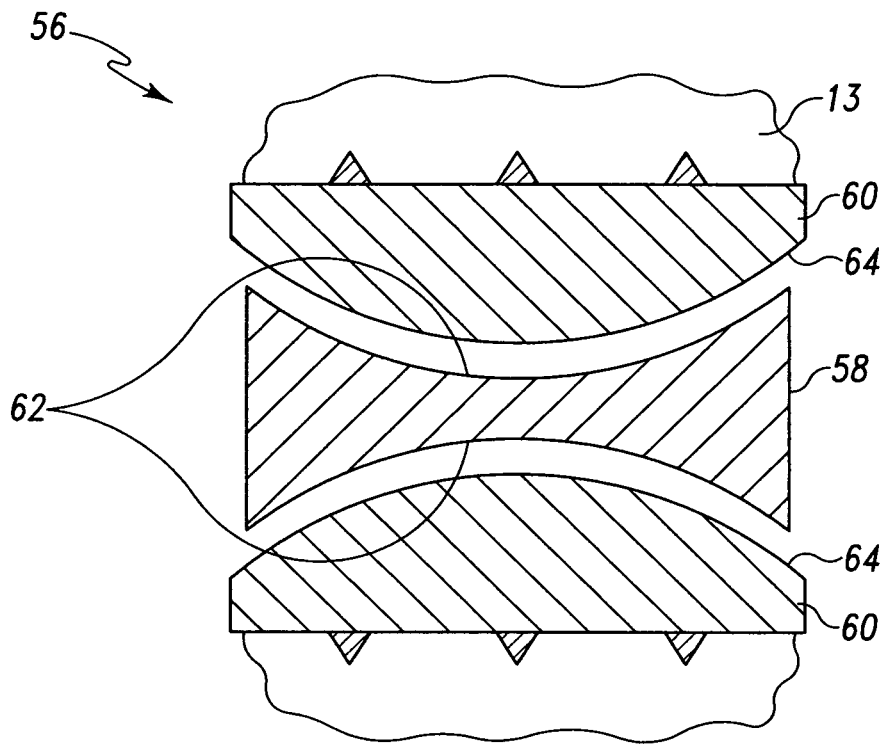
FIG. 18 is a partial plan view partially in cross-section of a vertebral orthopaedic implant for use in performing spine orthopaedic surgery that may be machined in accordance with yet another embodiment of the present invention.

Referring now to FIG. 18, yet another prosthesis that may be polished by the systems of the present invention, is shown as vertebral disc 56. The vertebral disc 56 includes a central component 58 and opposed end portions 60. The end portions 60 contact vertebrae 13 and the center portion 58 provides for the articulation of the vertebral artificial disc 56.

The central portion 58 includes a pair of opposed concave surfaces 62 while the end portions 60 include convex articulating surfaces 64. The concave surfaces 62 are suitable for being polished by the system 500 of FIG. 12 or the system 900C of FIG. 18C, while the convex surfaces 64 of the end portions 60 are suitable for polishing by, for example, the system 10 of FIG. 1 or the system 900B of FIG. 18B.

Figure 18A:
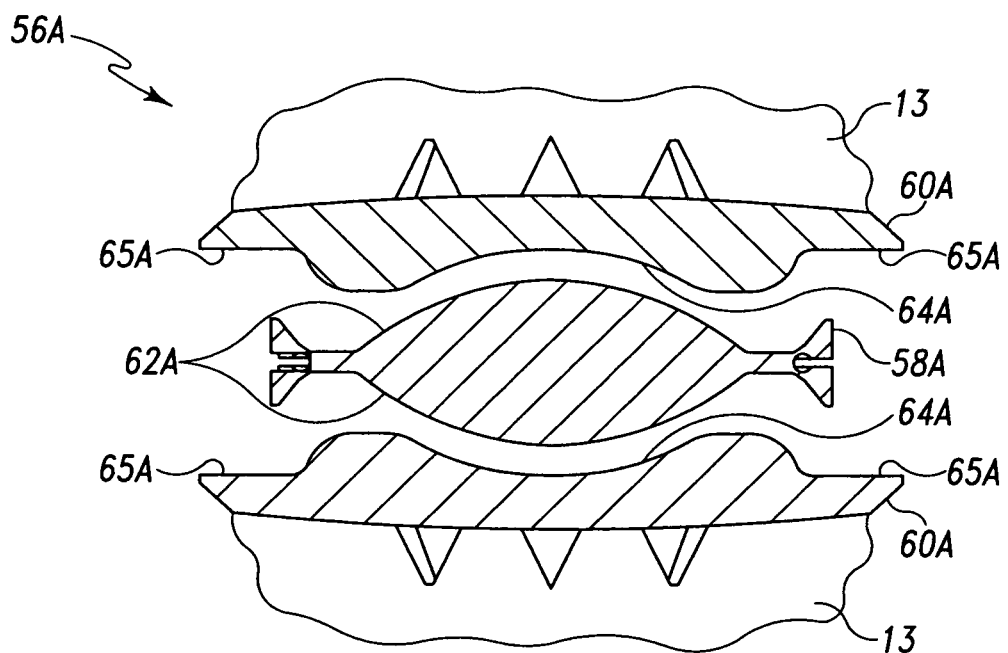
FIG. 18A is a partial plan view partially in cross-section of a Charite'® vertebral orthopaedic implant for use in performing spine orthopaedic surgery that may be machined in accordance with a further embodiment of the present invention.

Referring now to FIG. 18A, yet another prosthesis that may be polished by the system of the present invention is shown as Charite'® vertebral disc 56A. The vertebral disc 56A includes a central component 58A and opposed end portions 60A. The end portions 60A contact vertebrae 13 and the center portion 58A provides for articulation of the Charite'® vertebral artificial disc 56A.

The central portion 58A includes a pair of opposed convex surfaces 62A, while the end portions 60A include concave articulating surfaces 64A. The convex surfaces 62A and the concave articulating surfaces 64A include portions 65A that are substantially linear as well. The convex surfaces 62 of the central portion 58 are suitable for being polished by the system 10 of FIG. 1 or by system 900B of FIG. 18B. The concave surfaces 64A of the end portions 60A are suitable for polishing by, for example, the system 500 of FIG. 12 or the system 900C of FIG. 18C.

Figure 18B:
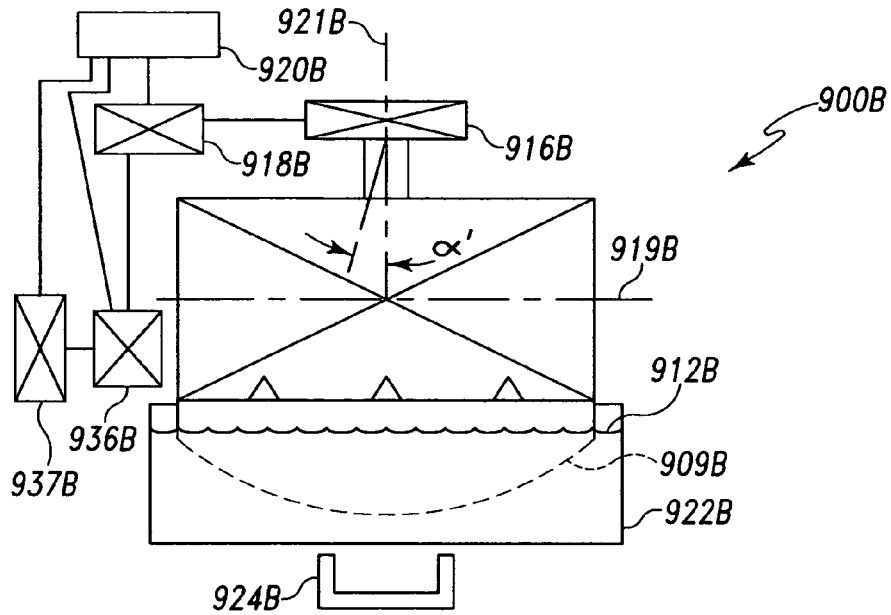
FIG. 18B is a schematic drawing of a polishing device for cooperation with the convex periphery of the outer components of the vertebral orthopaedic implant of FIG. 18 or with the convex periphery of the inner component of the Charite'® implant of FIG. 18A.

Referring now to FIG. 18B, yet another embodiment of the present invention is shown as system 900B. The system 900B is similar to the system 100 of FIG. 2, except that the system 900B is adapted for highly efficient polishing of convex work pieces. For example, the system 900 may be adapted for use in polishing convex articulating surfaces of vertebral implants, such as those described in FIGS. 18 and 18A.

For example, and as shown in FIG. 18B, the system 900B is adapted for use with, for example, work piece 909B in the form of a vertebral component. As shown in FIG. 18B, the system 900B includes a vessel 922B, which is in the form of a circular cup. The radius of curvature of the internal wall adjacent to the polishing zone (not shown) is larger than the largest radius of curvature of the vertebral component 909B.

During polishing, it is desirable to minimize the movement of the MP-fluid 912B relative to the vessel 922B. To minimize the movement or slippage of the MP-fluid 912B, the internal wall of the vessel may be covered with a layer or nap of porous material A (not shown). Work piece spindle 916B is connected with spindle slide 918B, which is connected to rotatable table 936B. The rotatable table 936B is connected to a table slide 937B.

Spindle slide 918B, rotatable table 936B, and table slide 937B may be driven by conventional servomotors, which operate according to electrical signals from programmable control system 920B. Rotatable table 936B permits work piece spindle 916B to be continuously rotated about its horizontal axis 919B, or permits its polishing at an angle α' with the initial vertical axis 921B of the spindle 916B. The horizontal axis 919B preferably is located at the center curvature located at the center of curvature of the polished surface at the initial vertical position of the work piece spindle 916B.

Work spindle slide 918B permits vertical displacement of the center of the polishing surface curvature relative to the horizontal axis 919B. Table slide 937B moves the rotatable table 936B with the spindle slide 918B and the work piece spindle 916B to obtain and maintain the desired clearance between the polished surface of the work piece and the bottom of the vessel 922B.

An electro magnet 924B may be stationery and positioned below the vessel 922B, such as its magnetic gap is symmetric about the work piece spindle axis 921B when this axis is perpendicular to the plane of the polishing zone.

Figure 18C:
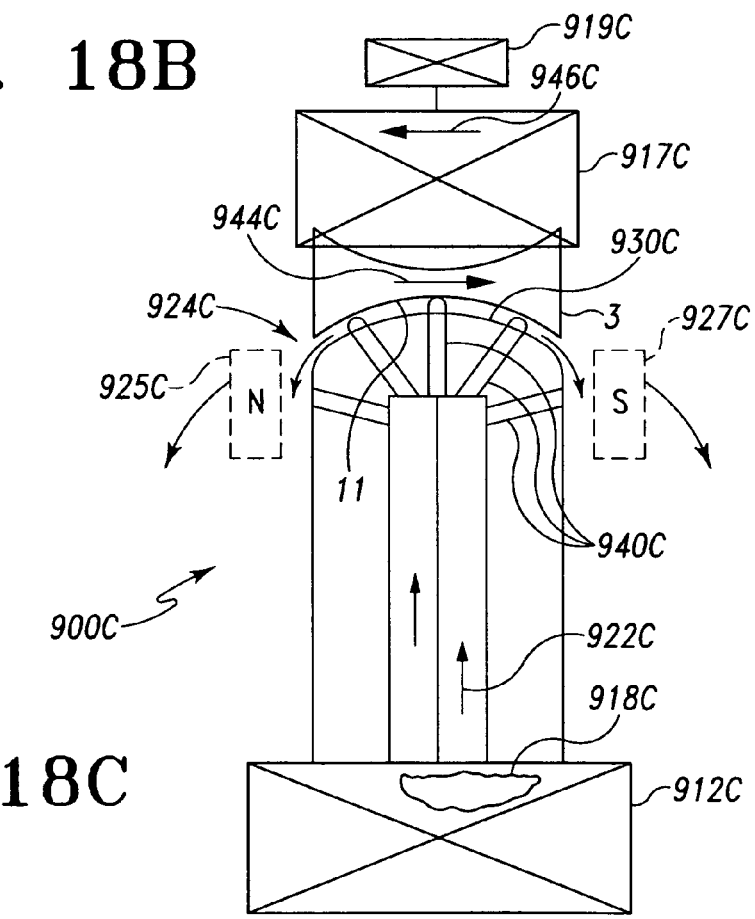
FIG. 18C is a schematic drawing of a polishing device for cooperation with the concave periphery of the central component of the implant of FIG. 18 or with the concave periphery of the outer components of the Charite'® implant of FIG. 18A.

Referring now to FIG. 18C, yet another embodiment of the present invention is shown as system 900C. The system 900C is adapted for use in polishing concave surfaces, for example, vertebral concave articulating surfaces. The system 900C is somewhat similar to the system 500 of FIG. 12, except that the system 900C utilizes a convex component 930C to replace the ball 530 of the system 500.

The system 900C includes a fluid conditioner 912C for receiving MP-fluid 918C. The fluid 918C is caused to flow along a fluid path 922C to polish zone 924C adjacent the articulating surface 11 of the vertebral component 3. The fluid path 922C includes a path through internal cavities 940C of the convex component 930C. The convex component 930C, as shown in FIG. 18C, includes the plurality of tubular or cylindrical cavities 940C, which permit the MP-fluid 918C to pass to the polishing zone 924C.

For the first type of MP-fluid the conditioner 912C may be in the form of a magnetic filter to separate the magnetic particles that have not deteriorated from those that have deteriorated and have lost their magnetic properties. The magnetic particles that have not lost their magnetic properties will be recirculated and those that have lost their magnetic properties will be removed. For the second type of MP-fluid the conditioner may merely measure the properties of the fluid and when the properties fall below a minimum level the MP-fluid may be drained and replaced.

Preferably, and as shown in FIG. 18C, the convex component 930C rotates in the direction of arrow 944C, while the vertebral component 3 is located and mounted on spindle 917C. The spindle 917C rotates in the direction of arrow 946C. The spindle 917C preferably rotates opposed to the direction of rotation 944C of the convex component 930C. The spindle 917C, as shown in FIG. 18C, may be permitted to translate vertically by means of spindle slide 919C. While the convex component 930C may successfully polish the vertebral component 3, without any angular motion between the vertebral component 3 and the convex component 930C, preferably the spindle 917C is able to rotate about the origin with a mechanism (not shown) such that additional portions of the convex component 930C may be positioned within the inner concave periphery 11 of the vertebral component 3. Such a mechanism is shown in FIGS. 12 and 12A.

System 900C of FIG. 18C further includes components capable of providing a magnetic field for the MP-fluid 918C. For example, and as shown in FIG. 18C, the system 900C of FIG. 18C includes a first pole 925C, which may be a north pole. The system 900C further includes a second pole 927C, which may be a south pole. The poles 925C and 927C may, for example, be electromagnetic magnets.

Figure 19:
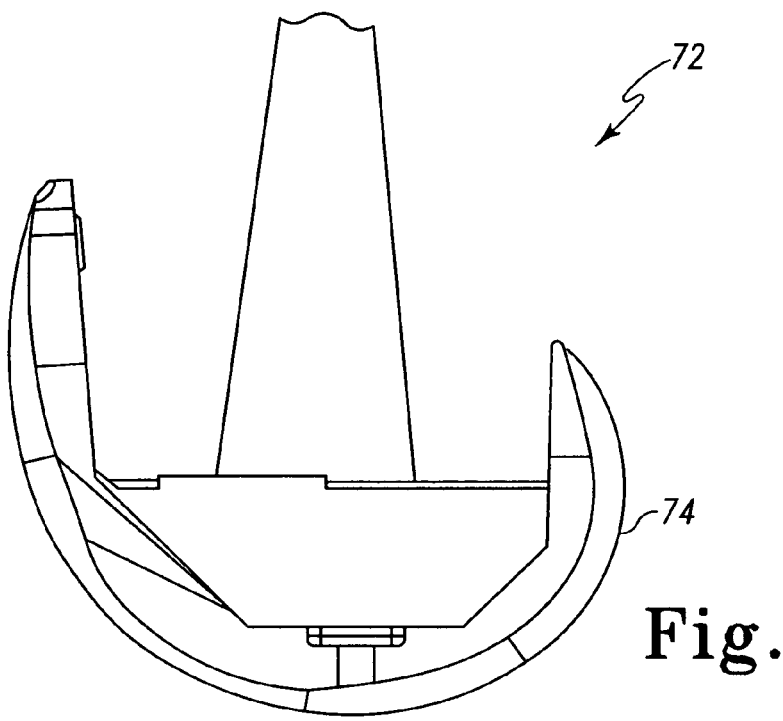
FIG. 19 is a partial plan view partially in cross-section of a knee femoral implant for use in performing knee orthopaedic surgery that may be machined in accordance with yet another embodiment of the present invention.

Referring now to FIG. 19, yet another prosthesis that may be polished by the system of the present invention is shown as femoral knee prosthesis 72. The femoral knee prosthesis 72 includes an articulating surface 74, which includes concave as well as convex portions. The convex portions of the articulating surface 74 are suitable for polishing by the system 10 of FIG. 1 while the concave portions are suitable for polishing by the system 500 of FIG. 12. It should be appreciated that, for simplicity, the entire articulating surface 74 may be polished utilizing the system 500 of FIG. 12.

Figure 19A:
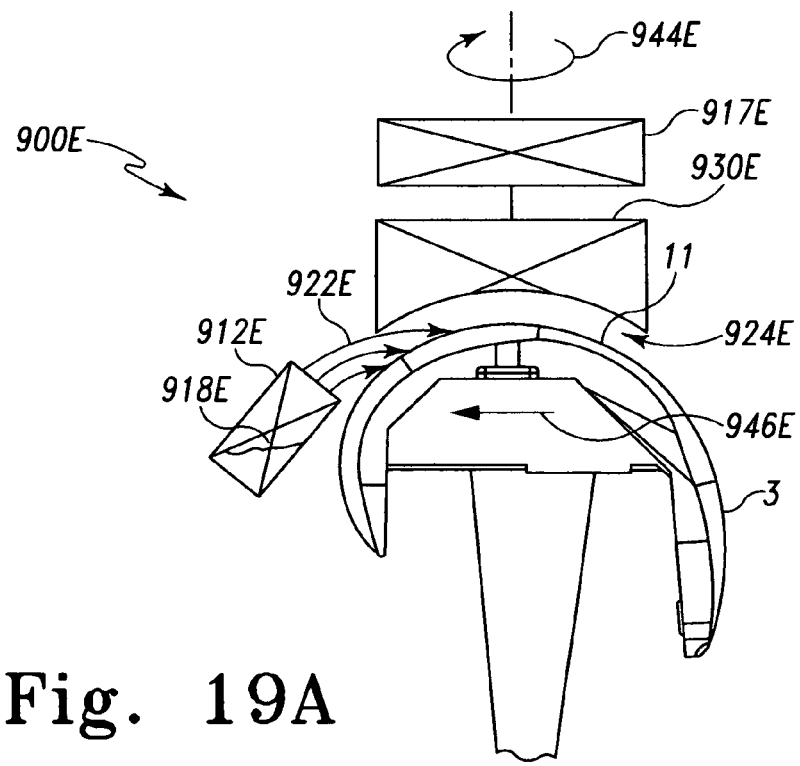
FIG. 19A is a schematic drawing of a polishing device for cooperation with the articulating arcuate periphery of the implant of FIG. 19.

Referring now to FIG. 19A, yet another embodiment of the present invention is shown as system 900E. The system 900E is adapted for use in polishing articulate surfaces, for example, knee femoral surfaces. The system 900E is somewhat similar to the system 10 of FIG. 1, except that the system 900E utilizes a reverse configuration to that of the system 10 in that the knee component 3 is positioned below and a concave component 930E is positioned over the knee component 3. The system 900E includes a fluid conditioner 912E for receiving the MP-fluid 918E. The MP fluid 918E is caused to flow along a fluid path 922E to polish zone 924E adjacent the articulating surface 11 of the knee component 3.

For the first type of MP-fluid the conditioner 912E may be in the form of a magnetic filter to separate the magnetic particles that have not deteriorated from those that have deteriorated and have lost their magnetic properties. The magnetic particles that have not lost their magnetic properties will be recirculated and those that have lost their magnetic properties will be removed. For the second type of MP-fluid the conditioner may merely measure the properties of the fluid and when the properties fall below a minimum level the MP-fluid may be drained and replaced.

Preferably, and as shown in FIG. 19A, the concave component 930E is mounted on spindle 917E rotates in the direction of arrow 944E, while the knee component 3 is located below. The knee component 3 rotates in the direction of arrow 946E. The knee component 3 preferably rotates in a direction opposed to the direction of rotation 944E of the concave component 930E.

While the concave component 930E may successfully polish the knee component 3, without any angular motion between the knee component 3 and the convex component 930E, preferably the spindle 917E is able to rotate, pivot or translate with a mechanism (not shown) such that additional portions of the knee component 3 may be positioned in alignment with the concave component 930E. Such a mechanism is shown in FIGS. 12 and 12A. Alternatively the mechanism may be a commercially available manipulator or robot (not shown).

Figure 20:
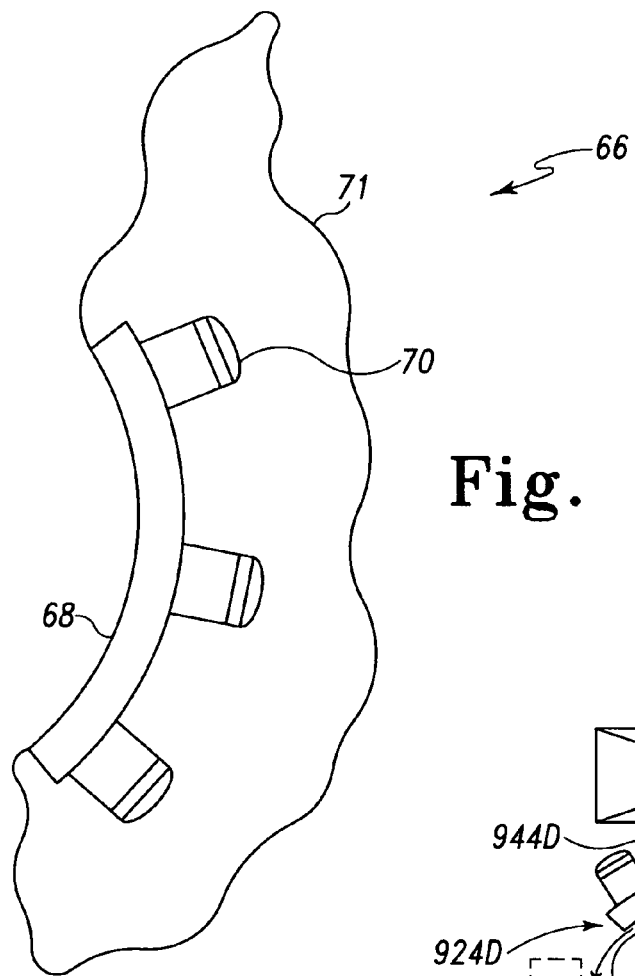
FIG. 20 is a partial plan view partially in cross-section of a glenoid implant for use in performing shoulder orthopaedic surgery that may be machined in accordance with yet another embodiment of the present invention.

Referring now to FIG. 20, yet another prosthesis that may be polished by the system of the present invention is shown as glenoid prosthesis 66. The glenoid prosthesis 66 includes a concave articulating surface 68 and opposed pegs 70, which engage with glenoid 71. The articulating surface 68 is adapted for polishing by the system 500 of FIG. 12.

Figure 20A:
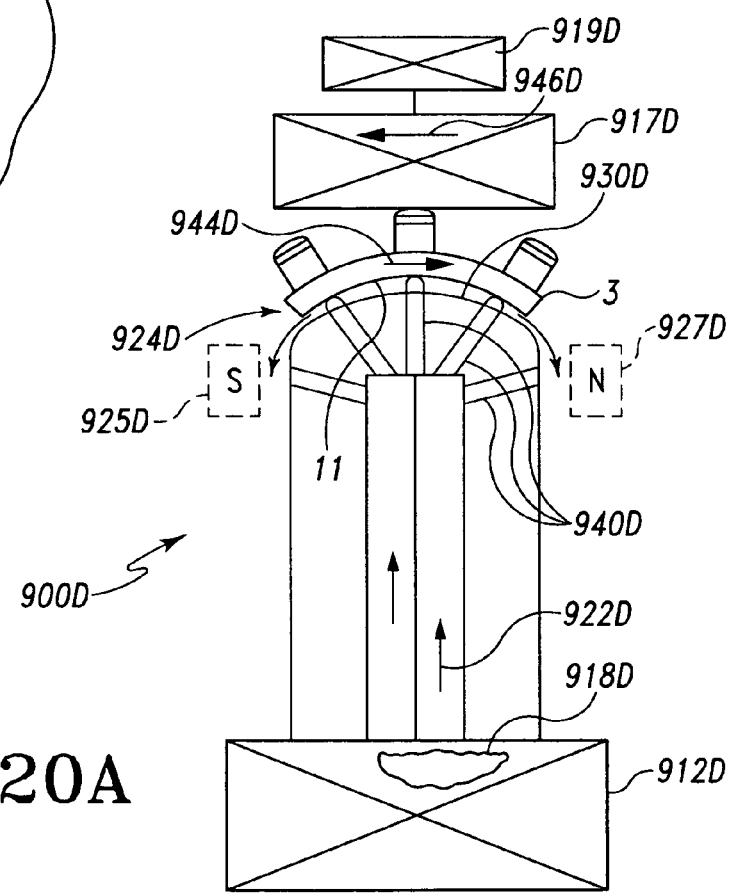
FIG. 20A is a schematic drawing of a polishing device for cooperation with the concave periphery of the implant of FIG. 20.

Referring now to FIG. 20A, yet another embodiment of the present invention is shown as system 900D. The system 900D is adapted for use in polishing concave surfaces, for example, glenoid implant surfaces. The system 900D is somewhat similar to the system 500 of FIG. 12, except that the system 900D utilizes a convex component 930D to replace the ball 530 of the system 500.

The system 900D includes a fluid conditioner 912D for receiving MP-fluid 918D. The fluid 918D is caused to flow along a fluid path 922D to polish zone 924D adjacent the articulating surface 11 of the glenoid component 3. The fluid path 922D includes a path through internal cavities 940D of the convex component 930D. The convex component 930D, as shown in FIG. 20A, includes the plurality of tubular or cylindrical cavities 940D, which permit the MP-fluid 918D to pass to the polishing zone 924D.

Preferably, and as shown in FIG. 20A, the convex component 930D rotates in the direction of arrow 944D, while the glenoid component 3 is located and mounted on spindle 917D. The spindle 917D rotates in the direction of arrow 946D. The spindle 917D preferably rotates opposed to the direction of rotation 944D of the convex component 930D. The spindle 917D, as shown in FIG. 20A, may be permitted to translate vertically by means of spindle slide 919D. While the convex component 930D may successfully polish the glenoid component 3, without any angular motion between the glenoid component 3 and the convex component 930D, preferably the spindle 917D is able to rotate about the origin with a mechanism (not shown) such that additional portions of the convex component 930D may be positioned within the inner concave periphery 11 of the glenoid component 3. Such a mechanism is shown in FIGS. 12 and 12A.

System 900D of FIG. 20A further includes components capable of providing a magnetic field for the MP-fluid 918D. For example, and as shown in FIG. 20A, the system 900D of FIG. 20A includes a first pole 925D, which may be a south pole. The system 900D further includes a second pole 927D, which may be a north pole. The poles 925D and 927D may, for example, be electromagnetic magnets.

Figure 21:
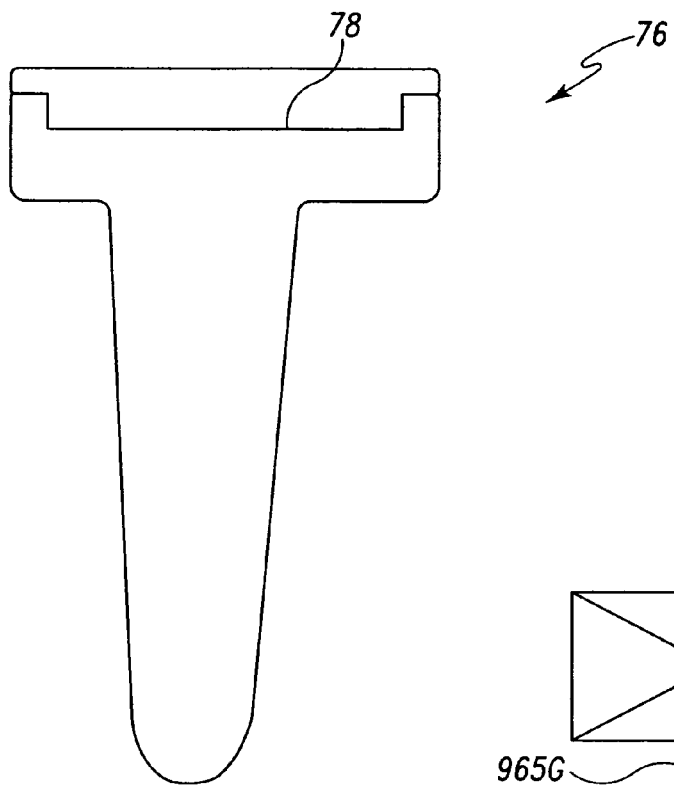
FIG. 21 is a partial plan view partially in cross-section of a knee tibial implant for use in performing knee orthopaedic surgery that may be machined in accordance with yet another embodiment of the present invention.

Referring now to FIG. 21, yet another embodiment of the present invention is shown as tibial tray 76. The tibial tray 76 includes a recess surface 78, which is suitable for polishing by any of the systems 600, 700 or 800 of FIGS. 13, 13A, and 13B respectively.

Figure 21A:
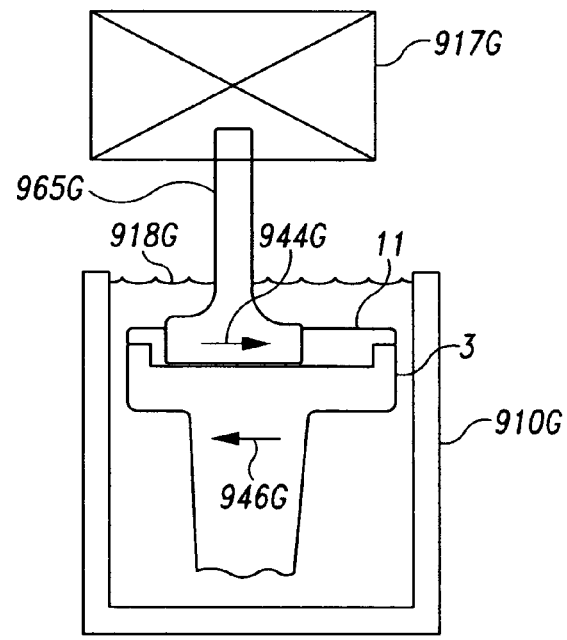
FIG. 21A is a schematic drawing of a polishing device for cooperation with the articulating periphery of the implant of FIG. 21.

Referring now to FIG. 21A, yet another embodiment of the present invention is shown as system 900G. The system 900G is adapted for use in polishing planar surfaces, for example, recessed knee tibial surfaces. The system 900G is somewhat similar to the system 100 of FIG. 2. The system 900G includes a vessel 910G for storing the MP-fluid 918G. The bearing surface of the recessed knee tibial component 3 is immersed in the MP-fluid 918G in the vessel 910G.

Preferably, and as shown in FIG. 21A, a planar contacting component 965G is mounted on spindle 917G and rotates in the direction of arrow 944G, while the recessed knee tibial component 3 is located below. The recessed knee tibial component 3 rotates in the direction of arrow 946G. The recessed knee tibial component 3 preferably rotates in a direction opposed to the direction of rotation 944G of the planar contacting component 965G.

System 900G of FIG. 21A further includes components capable of providing a magnetic field for the MP-fluid 918G. For example, the system 900G may include magnets such as those of FIG. 18C. The magnets may, for example, be electromagnetic magnets.

Figures 22, 22A:
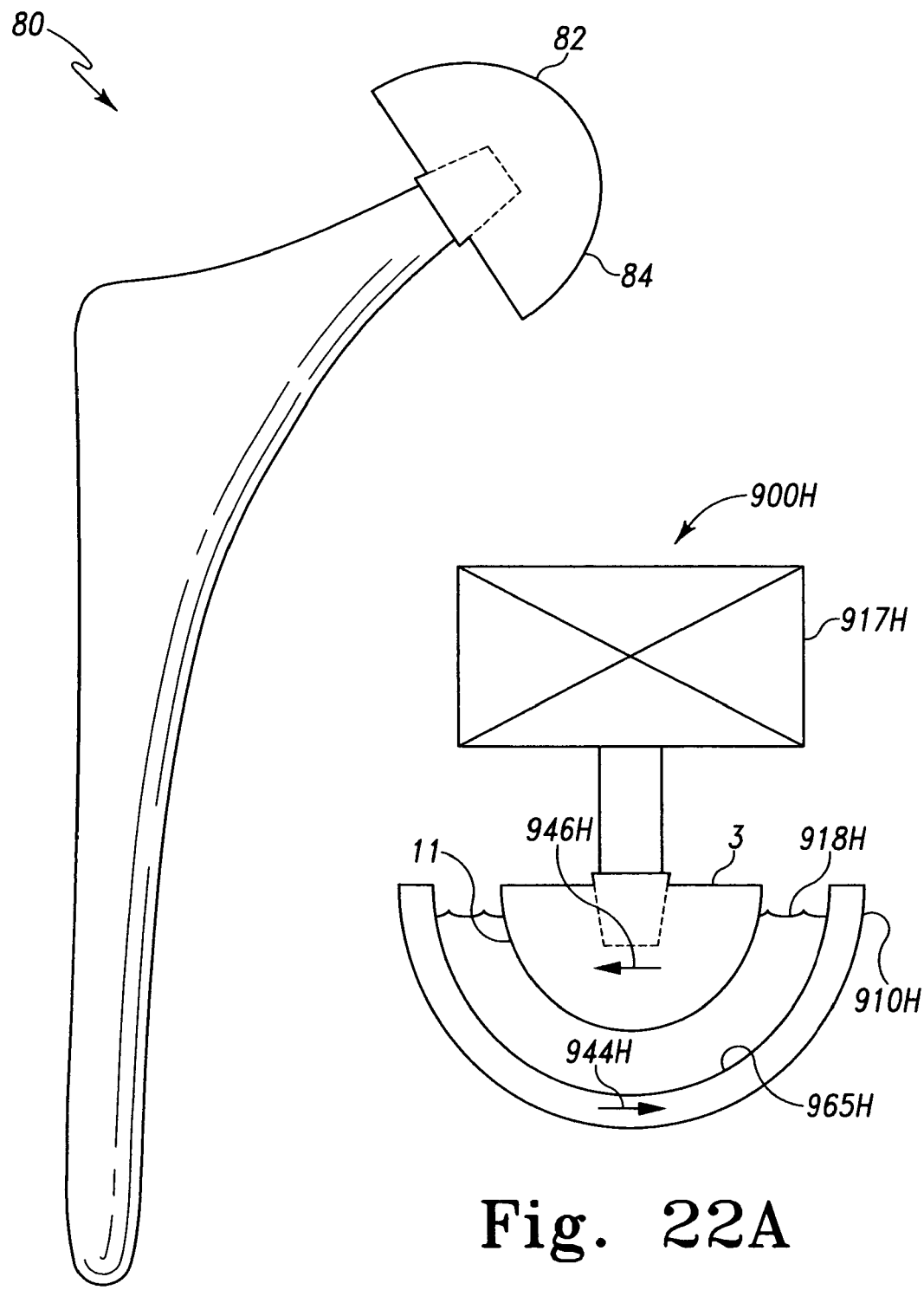
FIG. 22 is a plan view of a humeral implant for use in performing shoulder orthopaedic surgery that may be machined in accordance with yet another embodiment of the present invention.
FIG. 22A is a schematic drawing of a polishing device for cooperation with the articulating hemispherical periphery of the implant of FIG. 22.

Referring now to FIG. 22, yet another prosthesis that may be polished by the system of the present invention is shown as shoulder prosthesis 80. The shoulder prosthesis 80 includes a head 82, which may be removable from the shoulder prosthesis 80. The head 82 includes a convex articulating surface 84, which may be polished utilizing, for example, the system 10 of FIG. 1.

Referring now to FIG. 22A, yet another embodiment of the present invention is shown as system 900H. The system 900H is adapted for use in polishing convex surfaces, for example, humeral head surfaces. The system 900H is somewhat similar to the system 200 of FIG. 3. The system 900H includes a vessel 910H for storing the MP-fluid 918H. The bearing surface 11 of the convex humeral head component 3 is immersed in the MP-fluid 918H in the vessel 910H.

Preferably, and as shown in FIG. 22A, the vessel 910H has a concave periphery 965H. The vessel 910H may rotate in the direction of arrow 944H. The convex humeral head component 3 may be mounted on spindle 917H and rotates in the direction of arrow 946H. The convex humeral head component 3 preferably rotates in a direction opposed to the direction of rotation 944H of the vessel 910H.

System 900H of FIG. 22A further includes components capable of providing a magnetic field for the MP-fluid 918H. For example, the system 900H may include magnets such as those of FIG. 18C. The magnets may, for example, be electromagnetic magnets.

Figure 23:
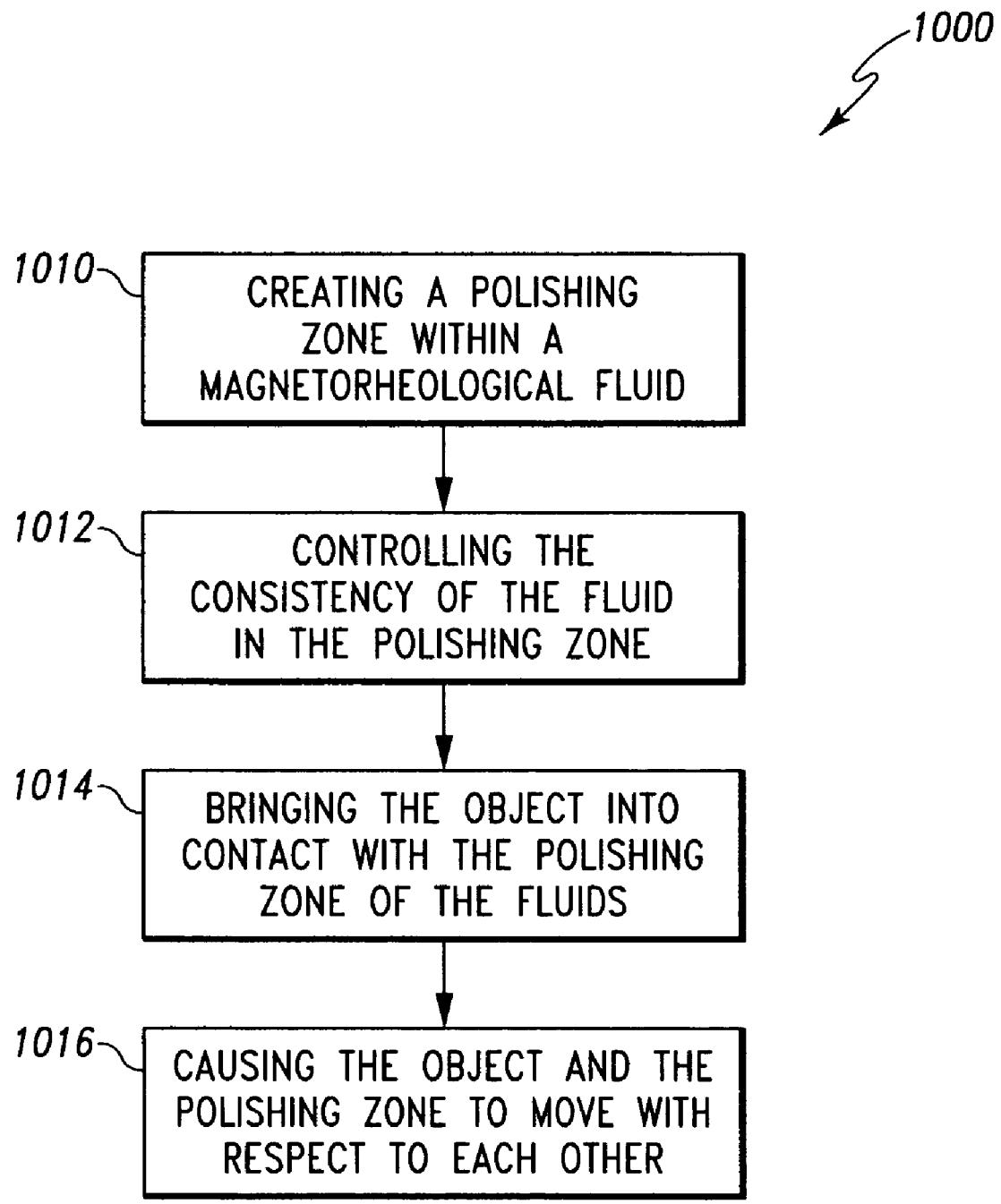
FIG. 23 is a process flow diagram of a method of preparing an articulating surface of a prosthetic component for use in joint arthroplasty surgery in accordance with yet another embodiment of the present.

Referring now to FIG. 23, yet another embodiment of the present invention is shown as method 1000 for polishing an articulating surface of an orthopaedic implant. The method 1000 includes a first step 1010 of creating a polishing zone within a MP-fluid. The method 1000 further includes a second step 1012 of controlling the consistency of the fluid in the polishing zone. The method 1000 further includes a third step 1014 of bringing the object into contact with the polishing zone of the fluid. The method 1000 further includes a fourth step of causing the object in the polishing zone to move with respect to each other.

Figure 24:
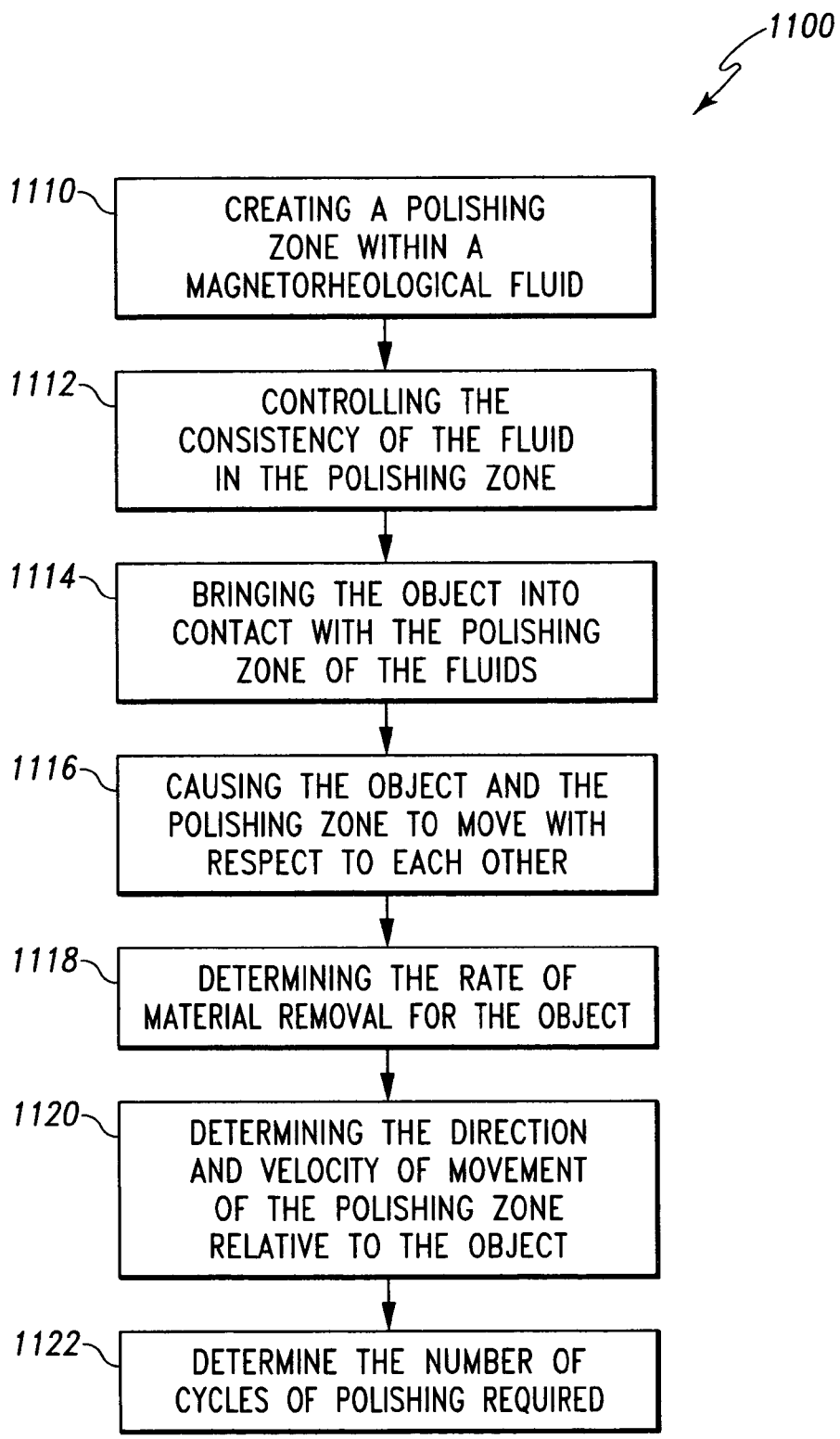
FIG. 24 is a process flow diagram for a yet another method of preparing an articulating surface of a prosthetic component for use in joint arthroplasty surgery according to a further embodiment of the present invention.

Referring now to FIG. 24, yet another embodiment of the present invention is shown as method 1100 of polishing an orthopaedic implant articulating surface. The method 1100 includes a first step 1110 of creating a polishing zone within a MP-fluid. The method 1100 further includes a second step 1112 of controlling the consistency of the fluid in the polishing zone. The method 1100 further includes a third step 1114 of bringing the object in contact with the polishing zone of the fluids. The method 1100 further includes a fourth step 1116 of causing the object and the polishing zone to move with respect to each other. The method 1100 further includes a fifth step 1118 of determining the rate material removal for the object. The method 1110 further includes a sixth step 1120 of determining the direction and velocity of movement of a polishing zone relative to the object. The method 1100 further includes a seventh step 1122 of determining the number of cycles of polishing required.

I claim:

1. A method of preparing a component of a prosthetic implant for use in orthopaedic surgery, comprising:
    forming a magnetorheological polishing fluid including nanoparticles coated in a two-stage microwave plasma synthesis process;
    providing the magnetorheological polishing fluid to a polishing zone;
    controlling the consistency of the magnetorheological polishing fluid in the polishing zone;
    bringing the component into contact with the magnetorheological polishing fluid in the polishing zone;
    causing the component and the magnetorheological polishing fluid in the polishing zone to move with respect to each other;
    monitoring the rate of material removal from the component;
    determining the direction and velocity of movement of the polishing zone relative to the component; and
    determining the number of cycles of polishing to be performed on the component.

2. The method of claim 1, wherein the determining the number of cycles of polishing comprises:
    determining the initial root means square height of surface irregularities of the component;
    determining the initial surface shape of the component; and
    determining the amount of material to be removed from the component during one cycle of polishing.

3. The method of claim 1, further comprising:
    using an interferometer to measure the surface form of the component;
    providing said measured surface form to a programmable controller; and
    comparing said measured surface form to a reference surface form or reference algorithm.

\* \* \* \* \*